US006796964B2

(12) United States Patent
Eidson et al.

(10) Patent No.: US 6,796,964 B2
(45) Date of Patent: Sep. 28, 2004

(54) AUTOMATIC VETERINARY MEDICAMENT DELIVERY SYSTEM

(75) Inventors: Wilbur L. Eidson, Minneapolis, MN (US); Jon Mathisrud, Inver Grove Heights, MN (US)

(73) Assignee: Eidson Associates, INC, Minneapolis, MN (US)

( * ) Notice: Subject to any disclaimer, the term of this patent is extended or adjusted under 35 U.S.C. 154(b) by 140 days.

(21) Appl. No.: 09/924,233

(22) Filed: Aug. 8, 2001

(65) Prior Publication Data

US 2003/0208157 A1 Nov. 6, 2003

Related U.S. Application Data

(63) Continuation-in-part of application No. 08/974,351, filed on Nov. 19, 1997, now abandoned.

(51) Int. Cl.[7] .................................................. A61M 5/20

(52) U.S. Cl. ......................... 604/135; 604/186; 604/191

(58) Field of Search .............................. 604/21, 30, 35, 604/45, 67, 72, 82, 118, 132, 135, 136, 137, 151, 155, 157, 183, 186, 191, 207, 224, 246, 290, 506, 131, 220, 187, 256

(56) References Cited

U.S. PATENT DOCUMENTS

| | | | | |
|---|---|---|---|---|
| 3,750,908 A | | 8/1973 | Bauerlein | |
| 3,949,746 A | | 4/1976 | Wallach | |
| 4,214,490 A | | 7/1980 | Chizek | |
| 4,226,235 A | * | 10/1980 | Sarnoff et al. | 604/136 |
| 4,228,930 A | | 10/1980 | Hogan | |
| 4,329,988 A | * | 5/1982 | Sarnoff et al. | 604/137 |
| 4,413,751 A | | 11/1983 | Tokorozawa | |
| 4,417,889 A | * | 11/1983 | Choi | 604/246 |

(List continued on next page.)

FOREIGN PATENT DOCUMENTS

| | | | |
|---|---|---|---|
| EP | 0 302 278 | * | 6/1988 |
| FR | 2 616 221 | * | 6/1987 |
| WO | WO 97/15185 | | 5/1997 |

OTHER PUBLICATIONS http://www.amp.com/.*

26 th New Zealand National Agricultural Fieldays Programme & Catalogue, Jun. 1994, p. 15.

28th New Zealand National Agricultural Fieldays Programme & Catalogue Jun. 1996, p. 79.

Exodax—20/50 Owners Manual p. 1–20.

Den Brok, L. I., New Zealand patent application # 221264, filed Jul. 30, 1987.

Whitford, New Zealand patent application # 224789 filed 1987, pub Oct. 27, 1989.

Engineering Dynamics LTD, New Zealand Patent Application 200968, filed Jun. 13, 1983.

*Primary Examiner*—Anhtuan T. Nguyen
(74) *Attorney, Agent, or Firm*—Janet Peyton Schafer

(57) ABSTRACT

An electrically powered, plunger-free, valve-free adjustable veterinary delivery system for the administration of veterinary pharmaceuticals or vaccines to a variety of poultry or livestock. The delivery system includes a rechargeable battery positioned to power an electric motor which is used to actuate a peristaltic pump that propels pre-determined quantity of fluid medicament through the system for delivery. The system teaches adjustable dosage control of the fluid medicament by means of an electronic control unit which uses photo-optic sensor to calibrate dosage. The veterinary delivery system includes several hand-held injection devices from which to choose, depending on desired use, each having a push-button trigger, at least one needle, a headlight, signal lights, optional dye marking means, and an optional mixing chamber for mixing medicaments at the time of delivery of the medicament, the hand-held injection devices being easily connected and disconnected by means of quick connect fluid couplers for being in fluid communication with the system and a nine-pin amp electrical connector for being in electronic communication with the control unit.

55 Claims, 13 Drawing Sheets

U.S. PATENT DOCUMENTS 4,469,481 A * 9/1984 Kobayashi .................. 604/67
4,473,173 A 9/1984 De Groff
4,547,189 A * 10/1985 Moore, Jr. .................. 604/136
4,670,007 A 6/1987 Wheeldon
4,817,599 A * 4/1989 Drews ........................ 606/107
4,888,004 A * 12/1989 Williamson et al. .......... 604/45
5,034,003 A * 7/1991 Denance ..................... 604/117
5,176,643 A * 1/1993 Kramer et al. ............. 604/135
5,242,083 A 9/1993 Christine
5,256,157 A * 10/1993 Samiotes et al. ........... 604/246
5,271,744 A * 12/1993 Kramer et al. .............. 604/506
5,273,524 A * 12/1993 Fox et al. ..................... 604/21
5,300,029 A * 4/1994 Denance ..................... 604/117
5,306,251 A * 4/1994 Alexander .................. 604/130
5,318,522 A * 6/1994 D'Antonio .................. 604/72
5,349,825 A 9/1994 Duke
5,451,210 A * 9/1995 Kramer et al. .............. 604/137
5,478,316 A * 12/1995 Bitdinger et al. ........... 604/135
5,578,014 A * 11/1996 Erez et al. .................. 604/192
5,580,347 A * 12/1996 Reimels ....................... 604/30
5,647,852 A * 7/1997 Atkinson .................... 604/151
5,662,612 A * 9/1997 Niehoff ...................... 604/155
5,840,071 A * 11/1998 Kriesel et al. ............. 604/132
5,921,963 A * 7/1999 Erez et al. .................. 604/192
5,928,197 A * 7/1999 Niehoff ...................... 604/155
5,961,494 A * 10/1999 Hogan ........................ 604/191
5,993,378 A * 11/1999 Lemelson ................... 600/109
6,017,322 A * 1/2000 Snoke et al. ............. 604/95.01
6,461,325 B1 * 10/2002 Delmotte et al. ............. 604/82
6,540,675 B2 * 4/2003 Aceti et al. ................. 600/309
6,562,013 B1 * 5/2003 Marasco, Jr. ............... 604/290
2001/0039398 A1 * 11/2001 Fowler et al. .............. 604/151
2002/0049415 A1 * 4/2002 Fukuda ....................... 604/191
2002/0077601 A1 * 6/2002 Kawagishi et al. ......... 604/224
2002/0120236 A1 * 8/2002 Diaz et al. .................. 604/151

* cited by examiner

AUTOMATIC VETERINARY MEDICAMENT DELIVERY SYSTEM

This is a continuation in-part application of Ser. No. 08/974,351, filed Nov. 19, 1999 now abandoned.

BACKGROUND

This invention relates to veterinary delivery devices for delivering medicaments, including pharmaceuticals or vaccines, to a plurality of poultry or other animals. In particular, this invention relates to a portable, electrically powered veterinary delivery system for reliably providing a precise amount of pharmaceuticals, or vaccine, rapidly to a plurality of fowl, porcine, ovine or other animals.

Injection devices are known in the art. Numerous injection devices have been provided in prior art that are adapted to include a manually operated plunger. A hand-held syringe, having a barrel and manually operated plunger, has been used to administer vaccines, antibiotics and other biological products. A problem with this device and method is that the accuracy of the dose is dependent on the manual strength and attention of the operator. When injecting large numbers of birds or other animals, the operator's hands become fatigued resulting in inaccurate doses being delivered to the bird or other animal being injected. An additional problem has been accidental injury to the operator as a result of either movement of the bird or other animal during the injection process or lack of lighting present at the barn or other injection locale. Injection into a human of veterinary products can cause permanent injury that may even result in amputation. Identifying which birds or other animals have been injected within a flock or herd has also been a problem.

While these units may be suitable for the particular purpose which they address, they would not be as suitable for the purposes of the present invention as hereinafter described.

SUMMARY

The present invention is directed to an automatic veterinary medicament delivery system that satisfies these needs for delivery of precise amounts of medicament to an individual animal or fowl. The medicament includes any fluid products for immunizing purposes or for treatment. The system provides rapid and consistent one-handed administration of the medicament, without fatigue-affected changes in the amount of medicament delivered, to large numbers of fowl, porcine, ovine, or other animals. An automatic veterinary medicament delivery system having features of the present invention comprises an electronic control unit having means for quickly adjusting the dosage of medicament to be delivered by injection. The veterinary delivery system includes several hand-held injection devices from which to choose, depending on desired use, each having a push-button trigger, at least one needle, a headlight, signal lights, optional dye marking means, and an optional mixing chamber for mixing medicaments at the time of delivery of the medicament, the hand-held injection devices being easily connected and disconnected by means of quick connect fluid couplers for being in fluid communication with the system and a nine-pin amp electrical connector for being in electronic communication with the control unit. One embodiment hand-held unit provides a single needle for injecting especially the ear of cattle. Another embodiment hand-held unit provides a single needle plus marking means. An additional hand-held unit provides two needles for injecting two unmixed medicines simultaneously. One embodiment hand-held unit provides a single needle, but the hand-held unit is inverted with a pistol grip attached for use especially with thick-skinned animals, such as cattle or pigs. All of these hand-held units provide means to deter self-injection of the user. In some hand-held units, this safety device is in the form of an emergency stop button. In an additional hand-held unit, a safety interlock is provided that prevents injection until a retractable resilient member is forced to a second, retracted position, to complete an electrical circuit permitting injection to take place. In all of these delivery systems, a source of fluid medicament, tubing interconnecting the injection devise and the medicament, an electrically powered pump in fluid communication with both the injection device and the medicament, actuation means for activating a pump forcing the medicament through the tubing from medicament source to the injection device for dispensing, are provided. A quick connect fluid coupler permits coupling of each hand-held unit to the pump. A nine-pin amp electrical connector connects the electrical power portion of each hand-held unit to the control unit. Also, a convenient carrying system is provided. Optional means for marking injected animals are also included. Methods for administering two medicaments simultaneously are also provided.

Manually depressing a trigger on the hand-held injection device of this delivery system, in conjunction with inserting a needle into the subject body, actuates the pump causing fluid to flow through the hollow needle accomplishing an injection. An emergency stop button is provided in case an error is made, ex. the needle goes through the ear, or through the ear and into the user's hand to prevent injection of a medicament into the user. This is an important deterrent to self-injection. An additional embodiment provides a safety interlock member which must be depressed to the needle hub to close the electrical switch which in turn actuates the pump causing fluid flow through the hollow needle only when the needle is fully inserted actuates an injection. This safety interlock is adjacent to the needle and positioned to extend to the length of the needle. This safety interlock is then depressed to the point adjacent to the needle hub as the needle is inserted. At this juncture, an internal extended rod from the safety interlock closes the electrical circuit by means of a Hall-effect switch. This, in turn, actuates the pump to cause fluid flow through the needle. This feature also deters accidental self-injection. Injection cannot take place until the needle is fully inserted, thus enabling the operator to withdraw an accidental stab prior to injection taking place. The goal of both of the systems is operator safety. Self-injection is a very serious accident among vaccinating crews.

The delivery system includes a means of marking, by automatically pressing an applicator pad containing a premeasured amount of dye pumped into it, in order to prominently and automatically mark each treated animal adjacent to the injection site.

The delivery system is powered by a compact, rechargeable 12-volt battery or 110 volt AC/12 volt DC converter, although other electrical means could be used, for sustained operation reducing fatigue and the likelihood of repetitive stress injury to the operator.

The delivery system includes a self-priming peristaltic pump for delivery of a consistent amount of medicament. The pump also reverses to retrieve unused medicament upon completion of each injection chore. The use of a peristaltic pump permits the system to be valve-free.

The delivery system has an optional head lamp at the injection site for greater safety and accuracy of injection.

The delivery system includes a green LCD on the handle to indicate that an injection is in progress. A red LCD on the handle indicates the medicament fluid is low.

The delivery system also includes an automatic counter to record and total the numbers of injections.

The delivery system also includes an optional mixing tube to combine medicaments.

The delivery system also includes a cleaning process to clean the tubing of the delivery system following each job. To accomplish cleaning, the pump switch on the face of the control unit is set to “forward” in order to circulate cleaning/sanitizing solutions for effective “clean in place”.

The system is enclosed in a back-pack or box, which protects it from dirt and dust and also provides a convenient place to store and transport the component parts.

It is the general object of the present invention to provide a novel and improved multiple dose veterinary delivery system that provides a precise dosage to a plurality of animals without requiring frequent refilling of the system between administrations of medicament to a plurality of animals.

A further object is to provide a veterinary delivery system which can be manipulated with one hand freeing up the second hand of the user to hold onto the subject animal for injection.

It is a further object to provide a veterinary medicament delivery system which ensures administration of precise amount of a medicament to the animal.

It is a further object of the invention to provide a veterinary delivery system that uses a self-priming pump.

It is a further object of the invention to provide a veterinary delivery system that eliminates waste of medicament and that provides an accurate count of doses delivered.

Another object is to increase the safety features of such an injection system by reducing the hazard of self-inoculation of the operator. A further object is to provide an easily transportable injection system.

Other objects and advantages will become apparent from the following detailed description and accompanying drawings.

BRIEF DESCRIPTION OF THE DRAWINGS

Understanding of the invention will be enhanced by referring to the accompanying drawings, in which like numbers refer to like parts in the several views and in which.

DETAILED DESCRIPTION OF THE CURRENTLY PREFERRED EMBODIMENTS

Understanding of the invention will be further enhanced by referring to the following illustrative but non-limiting example.

The term “medicaments” is intended to include serum, vaccine, antibiotics, and any other fluid products that may be used for immunizing or for treating poultry, bovine, ovine, porcine or other animals.

Overview

Figure 1:
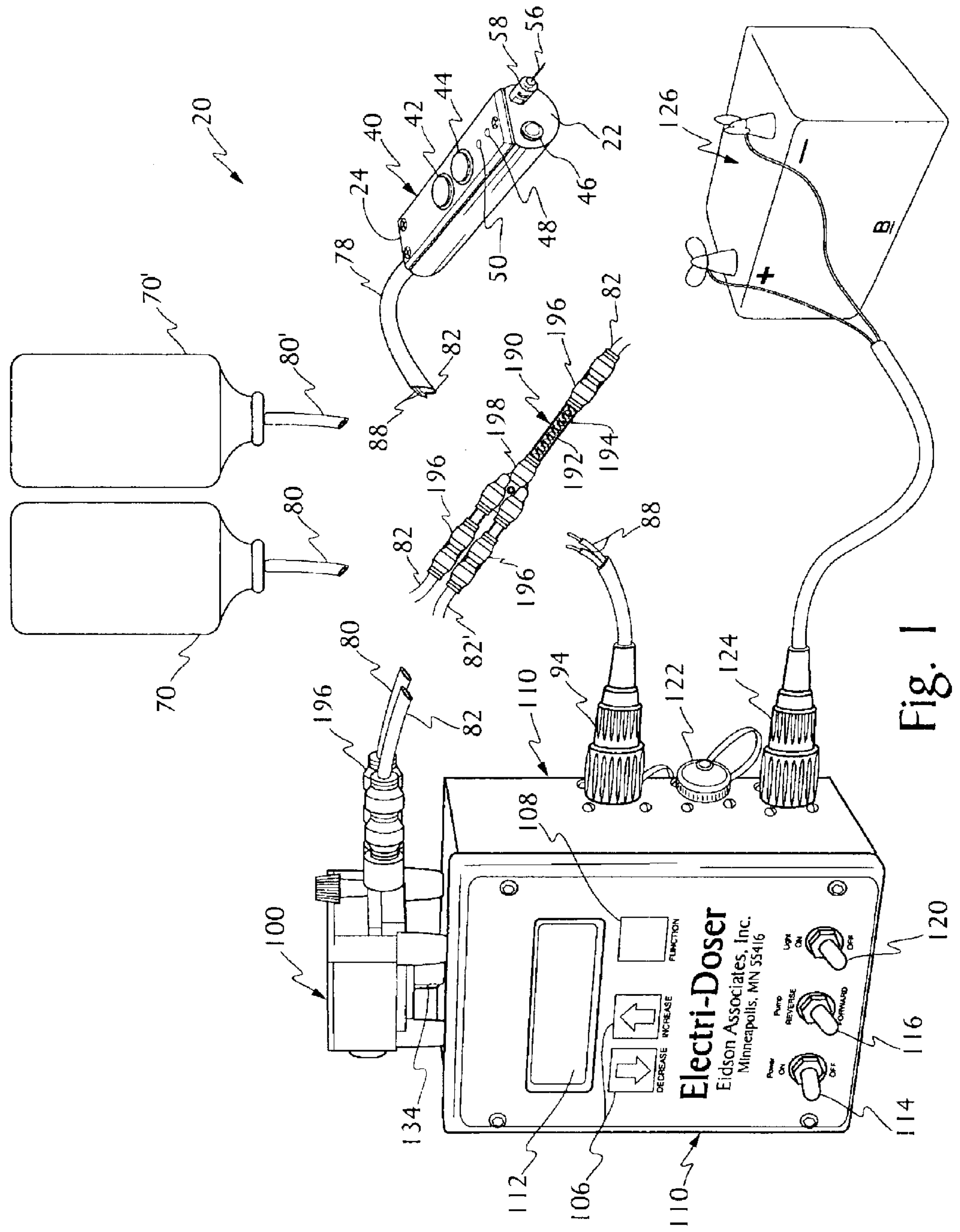
FIG. 1 is a plan view of the medicament delivery system of the current invention.
Figure 2:
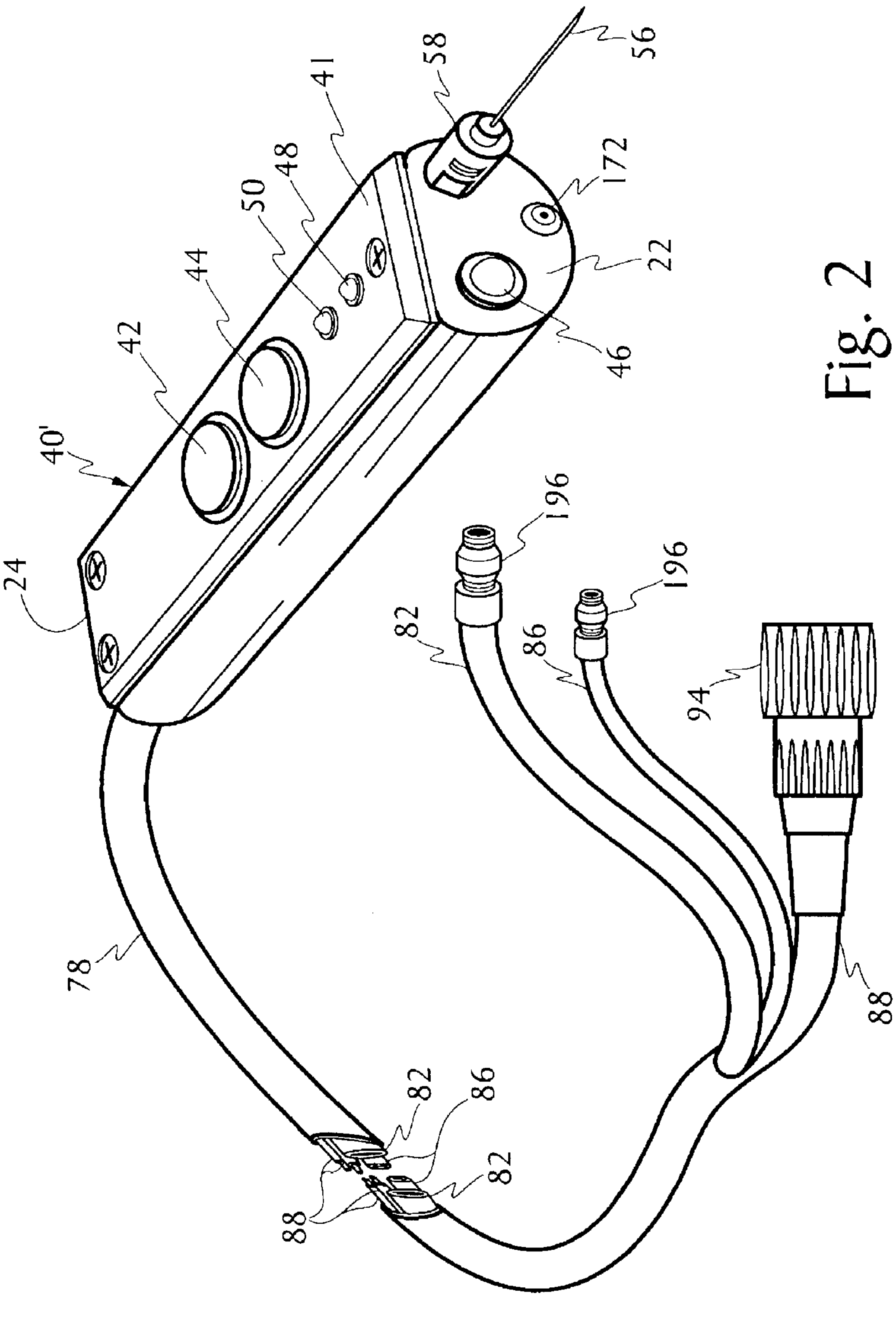
FIG. 2 is a perspective view of an embodiment hand-held unit of the medicament delivery system of FIG. 1.
Figure 3:
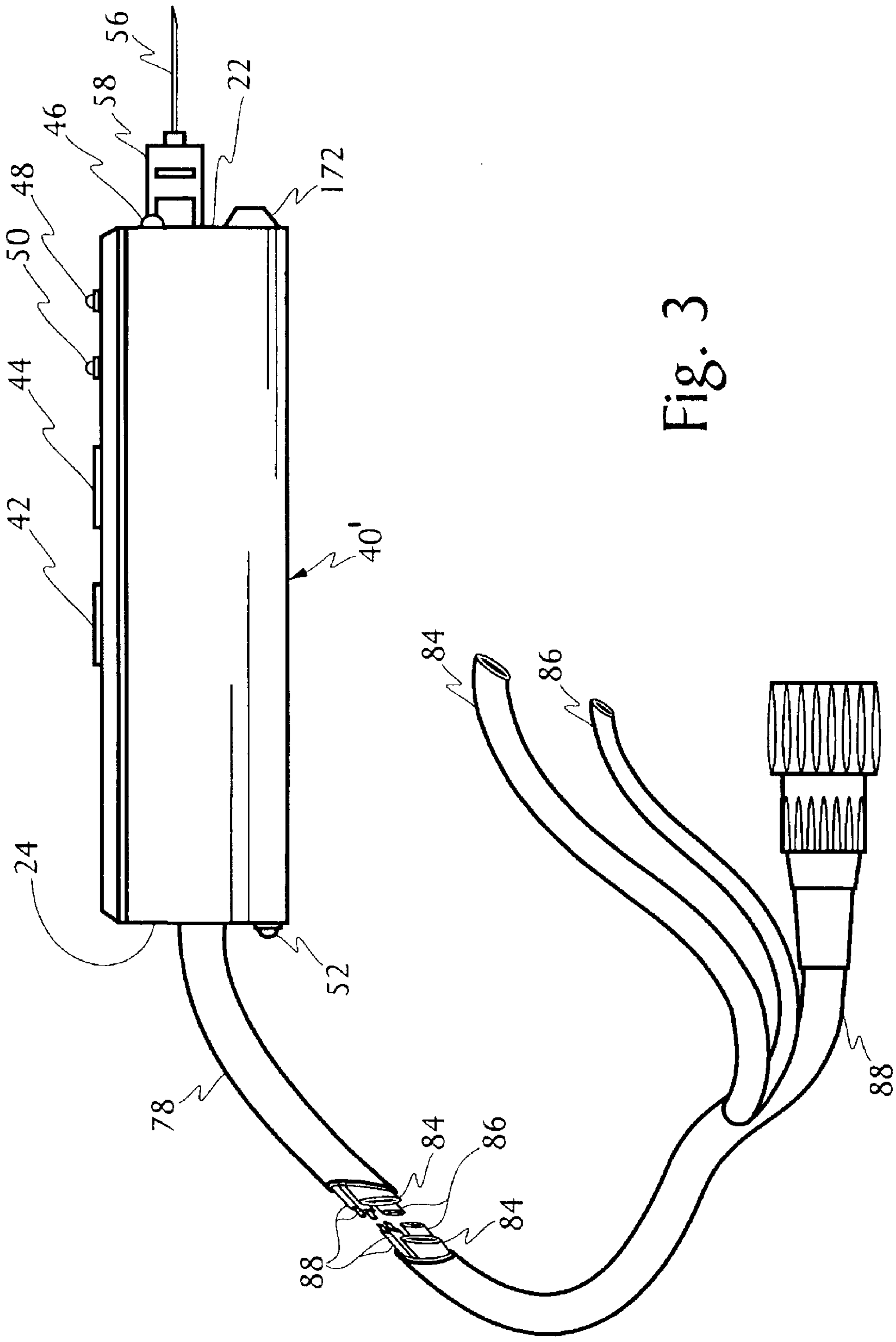
FIG. 3 is a side view of a hand-held unit of the medicament delivery system of FIG. 2.
Figure 5:
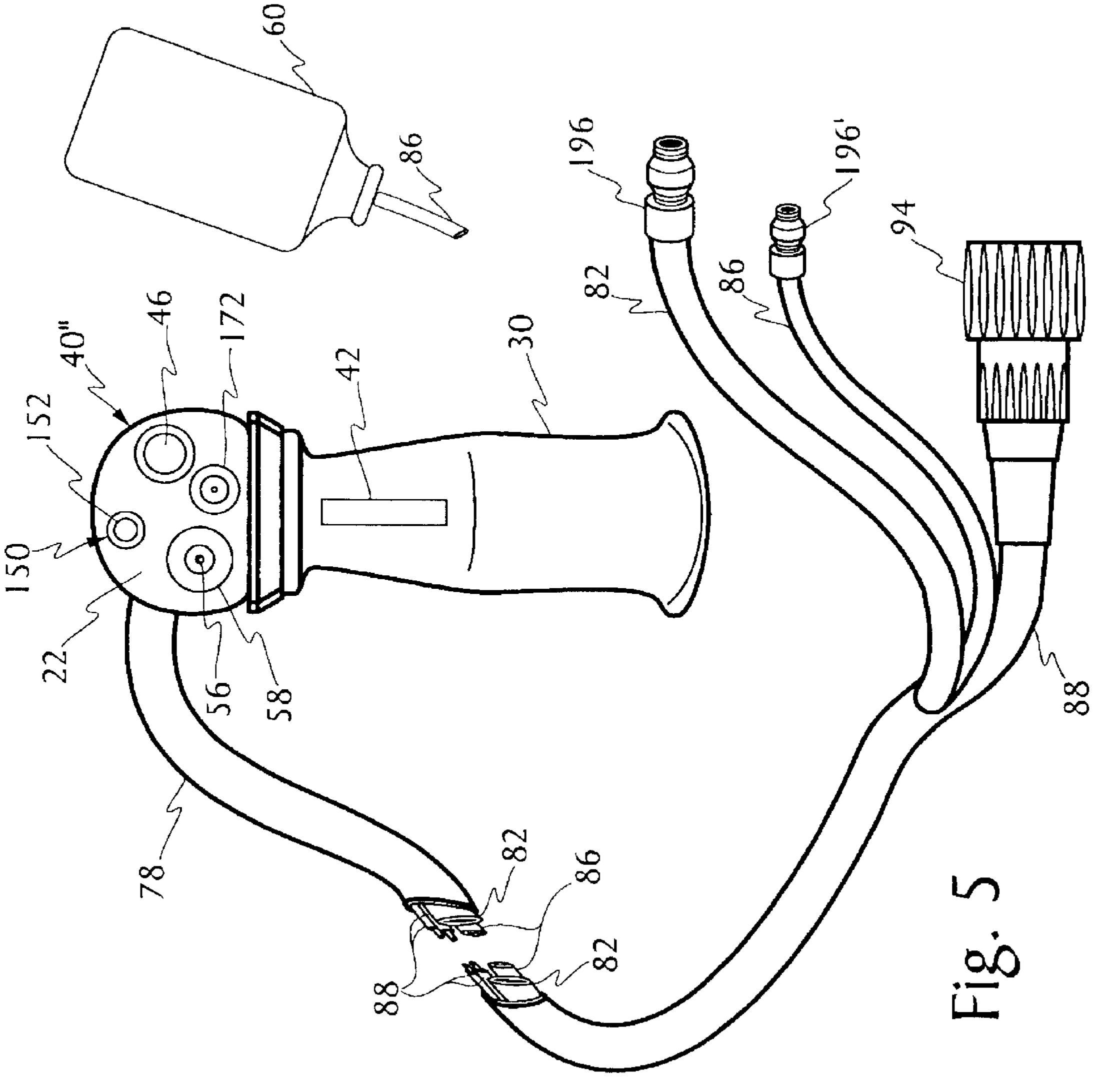
FIG. 5 is an end view of an alternate embodiment pistol grip hand-held unit.

Turning now to the drawings, in which like reference characters refer to corresponding elements throughout the several views, FIG. 1 illustrates an electrically powered automatic veterinary medicament delivery system shown generally at 20. System 20 is housed in a container such as a back pack and includes a hand-held unit 40 in fluid communications, by means of conduit tubing 78, with a medicament container 70. A first embodiment hand-held unit 40, has a single needle 56, no dye means, is especially for use in injection of a medicament into the ear of a bovine. All of die hand-held units 40 have a generally cylindrical shape with a flattened surface 41 on which, in embodiments are mounted both a trigger 42 and an emergency stop 44 button. An additional embodiment also has a trigger but no emergency stop. Also shown are a green LCD 48, which lights to indicate an injection is in progress, and a red LCD 50 which lights to indicate that the medicament level is low. The “function” key pad 108 is touched on the control unit 110 to set the anticipated number of total count so that the low medicament bottle LCD lights up at the appropriate time, ex. when 90% of the doses have been given. Head lamp 46 is used to illuminate the area of injection, as well as an optional dye pad 172 along with die needle mount 58, in actual use, a Luer lock, all mounted on a proximal surface 22 of the hand-held unit 40'''. Entering this distal end 24 of hand-held unit 40''' is tubing 82 containing medicament 84, dye 86 and electrical power cords 88. All of the various hand-held unit embodiments 40, 40', 40'', & 40'''' look and work similarly. A pump 100, which sits atop a control unit 110, sucks up the medicament from within medicament container 70 through tubing 80 and forces the fluid medicament from pump 100 exiting through tubing 82 and continuing through conduit tubing 78 for delivery by the hand-held unit 40 through a hollow needle 56. The control unit 110 utilizes an electronic dosage control 130, shown in detail in FIG. 7, to deliver a predetermined precise amount of medicament upon injection. Additionally, the electronic dosage control 130 provides means of changing the dosage of these predetermined precise amounts of medicament. Control unit 110 also provides optional marking means. Marking dye, in an optional embodiment shown at FIGS. 2,3,& 5, is delivered through dye means, such as by an applicator pad 172, simultaneously with injection of the medicament, marking the individual poultry, porcine, ovine or other animal injected. Control unit 110 function keypad 108 has an on/off control of dye means. Control unit 110 also provides for counting the number of injections made.

Figure 4:
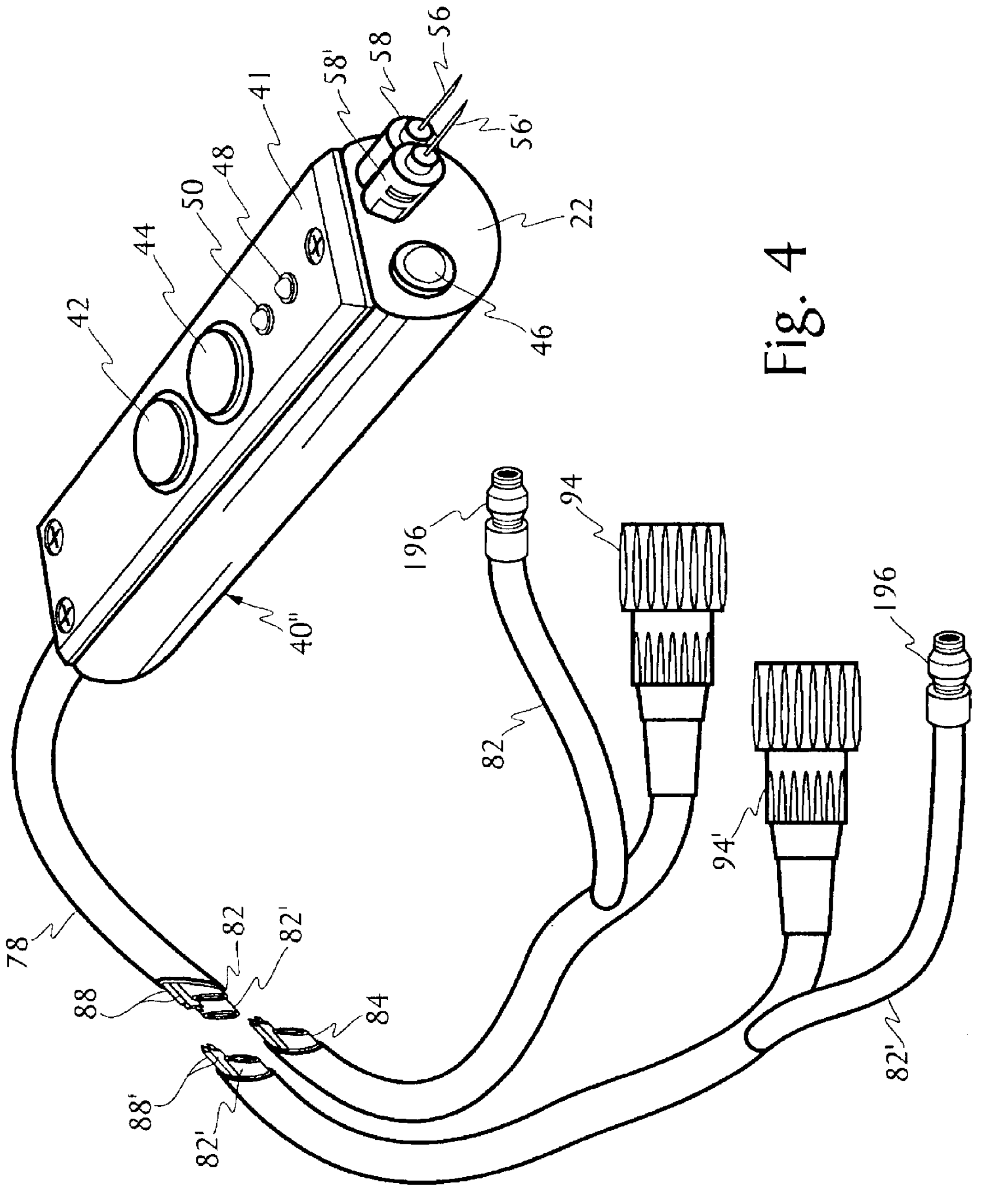
FIG. 4 is a side perspective view of an additional embodiment hand-held unit of the medicament delivery system of FIG. 1.
Figure 8:
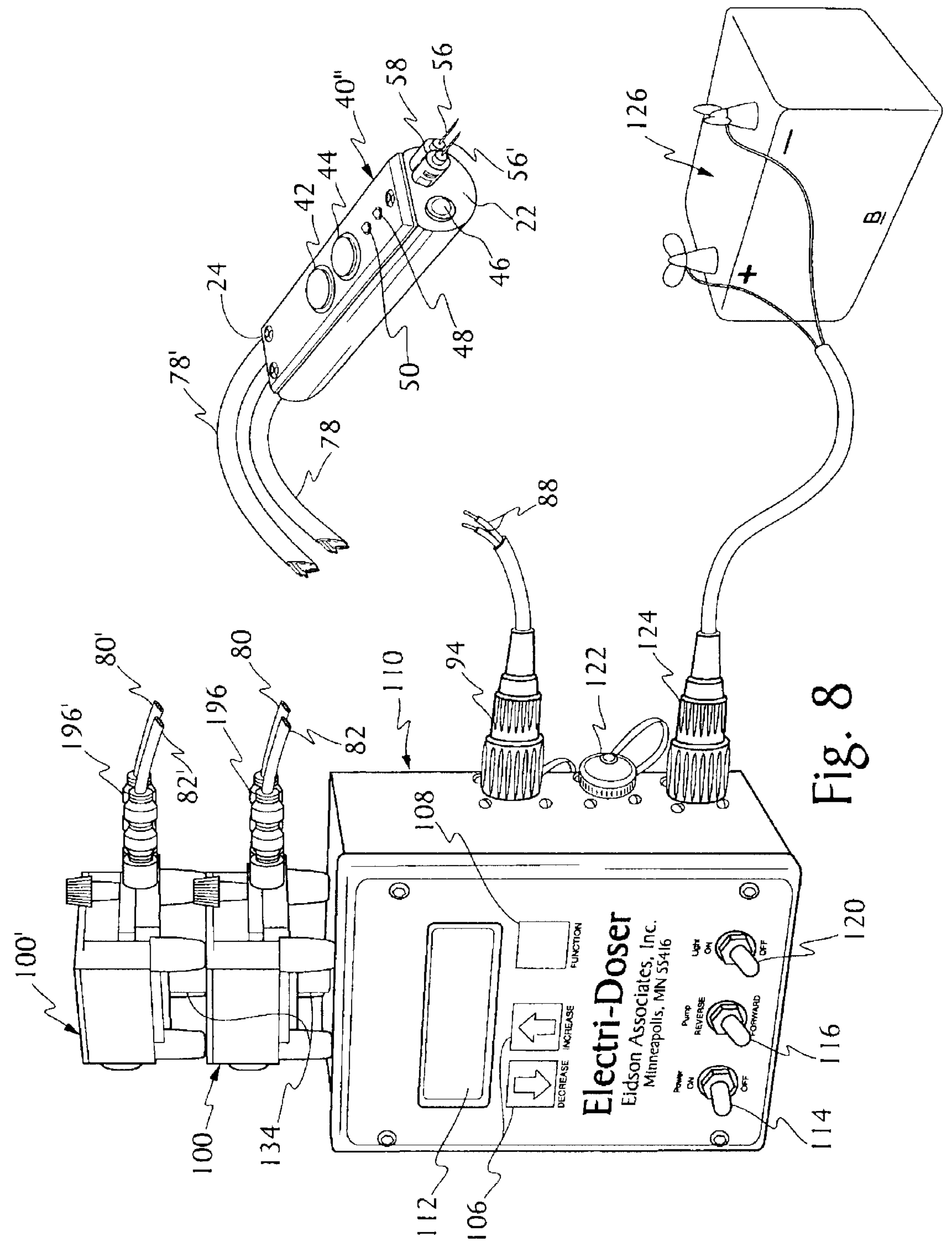
FIG. 8 is a plan view of an alternate embodiment hand-held unit where two medicaments are pumped through two pumps simultaneously at the same rate.
Figure 9:
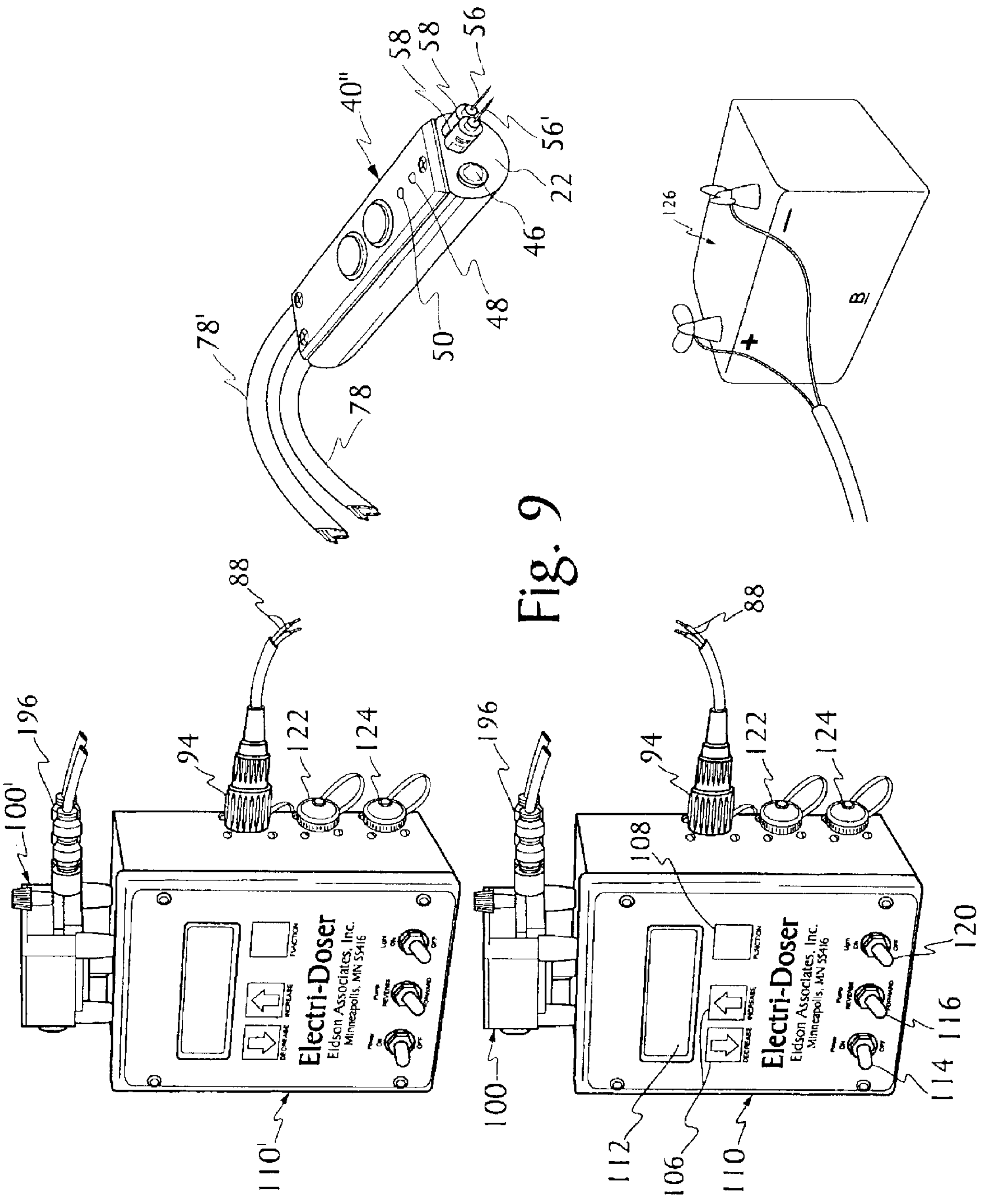
FIG. 9 is a plan view of an alternate embodiment hand-held unit where two medicaments are pumped through two separate control units at differing rates.
Figure 10:
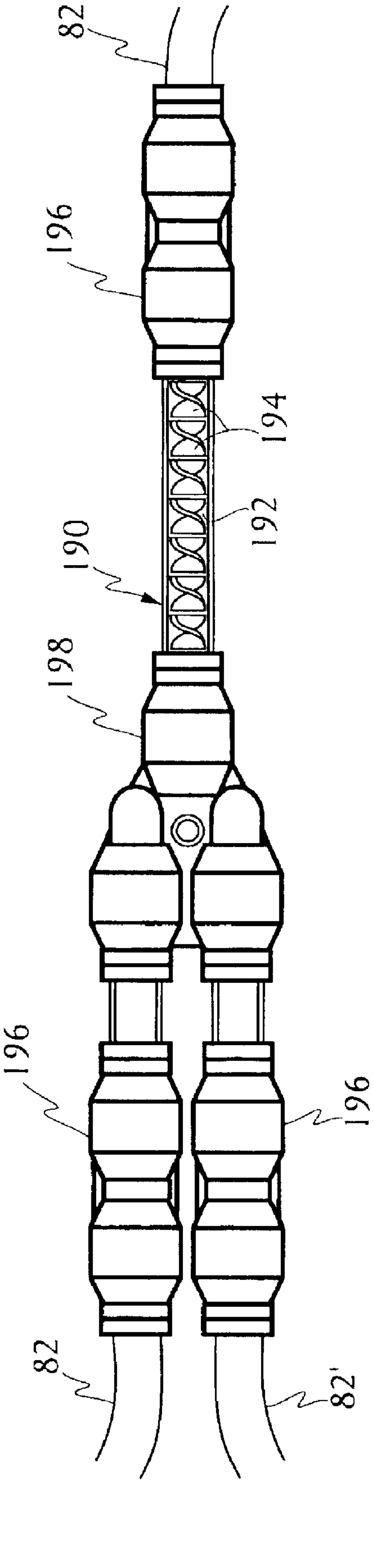
FIG. 10 is a plan view of the medicament mixing tube.

In all of the disclosed embodiments, fluid from more than one medicament container 70 can be injected simultaneously through their respective tubing 80, the medicaments forced by the pump 100, through an optional mixing tube 190, shown in detail in FIG. 10, intermixing the two medicaments prior to their being injected through the selected hand-held unit 40, 40', 40", 40'" or 40"". Additionally, in all of the embodiments, fluid from more than one medicament container 70, 70' can be injected simultaneously. Where different dosages are needed, two control units 110, 110' with the associated pumps 100, 100' can be connected up to a single hand-held unit 40, 40', 40" 40" or 40"" for simultaneous injection, either after mixing the medicaments and injected through hand-held unit 40 40" and 40'", or when the medicaments cannot be mixed for whatever reason, by injecting simultaneously through two needles through hand-held unit 40' as shown in FIG. 4. Once the requirements are determined, which medicaments are to be injected, can they be mixed, if not, are they administered at the same dosage, the appropriate hand-held unit 40, 40', or 40" is selected and electronically connected to control unit 110 by the Amp connector 94, attached to the end of conduit tubing 78 and in fluid communication by means of a quick connect fluid connector 196 at the end of each tubing 82, 76,. If the medicaments may be mixed, the mixing tube 190 must be attached to the tubing 82 by quick connect fluid couplers 196. Quick connect fluid couplers 196 are also mounted on pump 100 to attach tubing 80 to medicament container 70. If more than one pump is needed but the medicament to be administered can be given at the same dosage, then a two pump system 100, 100', such as shown in FIG. 8, is used. Hand-held unit 40, 40' or 40'" may be used. When the medicament to be administered is not of the same dosage, and cannot be mixed, then two control units 110, 110' must be used, such as shown in FIG. 9, then hand-held unit 40" is selected and connected to both control units 110,110' by means of conduit tubings 78, 78'. A nine-pin amp connector 94 connects the electronic control unit 110 to any of the hand-held units 40. A four-pin amp connector 122 connects the electronic control unit 110 to the dye pump. Another four-pin amp connector 124 connects the control unit 110 to the battery 126. These different types of amp connectors protect against accidental connection of the wrong device to the outlet at the control unit 110.

The control unit 110 sets the dosage, the injection count, the anticipated number of total count so that the low medicament bottle LCD lights up at the appropriate time, and optional marking dye by means of touching the display LCD for each function, by pushing the "Function" keypad 108 and using the up and down arrows 106 to select the appropriate choice, dose, injection count, low bottle warning and marking dye.

As shown in FIG. 1, the electrically powered automatic veterinary medicament delivery system is set for injecting ears of cattle. While the hereinafter described safety interlock could be added to this hand-held unit 40, it is not felt to be necessary when injecting ears of cattle. The ears are injected, by the way, to prevent damage to an edible portion of the cattle.

The power source for running any embodiment of this system is a re-chargable battery although plugging into the circuitry of the barn or other housing could be used.

FIG. 2 is a side perspective view of second embodiment hand-held unit 40' of the medicament delivery system 20, having a single needle 56 and dye pad applicator 172. In this view, hand-held unit 40' has a generally cylindrical shape with a flattened dorsal surface 41 on which are mounted both a trigger 42 and an emergency stop 44 button. Also shown are a green LCD 48, which lights to indicate an injection is in progress, and a red LCD 50 which lights to indicate that the medicament level is low. The "function" key pad is touched on the control unit 110 to set the anticipated number of total count so that the low medicament bottle LCD lights up at the appropriate time, ex. when 90% of the doses have been given. Head lamp 46 is used to illuminate the area of injection, as well as an optional dye pad 172 along with the needle mount 58, in actual use, a Luer lock, all mounted on a proximal surface 22 of the hand-held unit 40'. Entering this distal end 24 of hand-held unit 40' is tubing 82 containing medicament 84, dye 86 and electrical power cords 88. This hand-held unit 40' is especially for use in injection of a medicament into a bovine at a point other than the ear. Marking means conspicuously mark the animal as it is injected. Quick connect fluid couplers 196 are mounted on the terminal ends of both medicament tubing 82 and dye tubing 86 to permit quick, convenient connection of this particular hand-held unit 40" to control unit 110.

FIG. 3 is a side view of the hand-held unit 40' of the medicament delivery system of FIG. 2 showing an additional light 52 indicating that an injection is in progress.

FIG. 4 is a side perspective view of an alternate embodiment hand-held unit 40" of the medicament delivery system of FIG. 1. This embodiment has the same general shape as the first embodiment, namely hand-held unit 40" having a generally cylindrical shaped body with a flattened dorsal surface 41 on which are mounted both trigger 42 and an emergency stop 44 button. This embodiment adds a second needle 56' and needle mount 58' Luer lock to the proximal surface of the hand-held unit 40". Although the optional dye applicator pad is not shown, it will be understood that this dye applicator pad is an option on all of the hand-held units. Also not shown in this view but understood to be mounted on the hand-held unit 40" is an additional light indicating that an injection is in progress similarly to light 52 in FIG. 3. Two needles 56, 56' are needed with this embodiment because two medicaments that may not be mixed are being injected, as indicated by the two medicament tubings 82, 82'. Quick connect fluid couplers 196 are mounted on the terminal ends of both medicament tubings 82, 82' and dye tubing 86, 86' to permit quick, convenient fluid connection of this hand-held unit 40" to control unit 110. If the dosage is the same for both medicaments, a second pump 100' can be mounted atop the first pump 100, as shown in FIG. 8, connected to a hand-held unit 40". The two pumps, 100, 100' piggy backed atop the other, are interconnected by an drive shaft 134 whereby the pumps turn at the same rate of speed delivering identical amounts of medicament. If, however, different dosages of the two medicaments is needed, due to differences in viscosity or potency, or the like, two control units, 110, 110' would be needed, as shown in FIG. 9. The tubing from both units would be combined so only one hand-held unit 40" is needed. Although only one processing of the subject animal occurs, two injections of different un-mixed medicaments are given simultaneously to the same subject animal.

Figure 13:
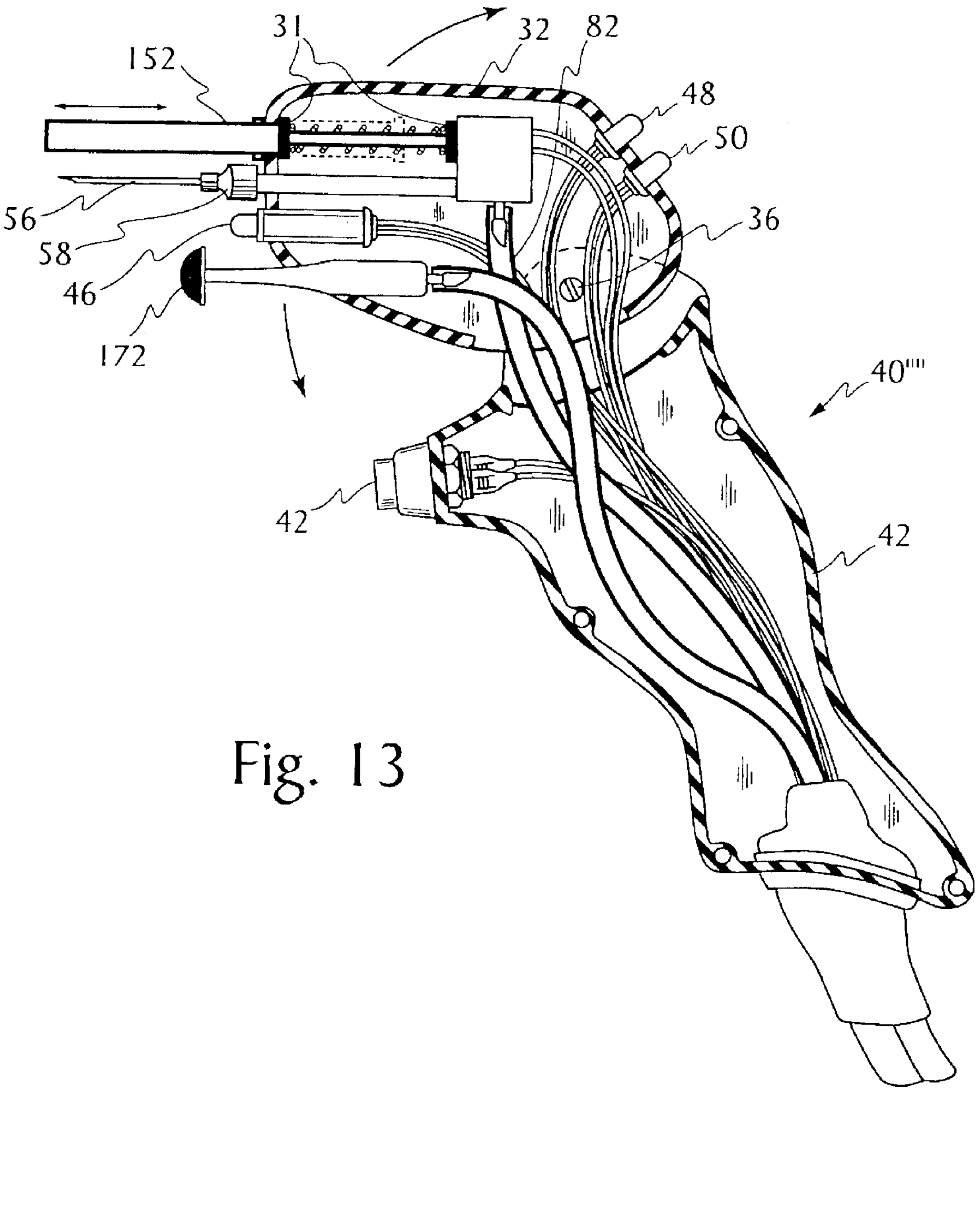
FIG. 13 is a side view of an additional embodiment, pivoting hand-held unit, with certain portions shown in cross-section.

FIG. 5 is an end view of a fourth embodiment hand-held unit 40'" which has a pistol grip 30. In this embodiment, the generally cylindrically shaped hand-held unit 40'" is basically turned upside down so that the flattened surface is on the ventral side. The trigger 42 is mounted on the front surface of the pistol grip 30 for convenience of the user. This embodiment has the same elements on the proximal surface 22, namely a needle mount 58, a hollow needle 56, an optional dye means 170, with associated dye tubing 86, and headlight 46. Added to this embodiment is safety interlock 150 which consists of a solid member 152, which when forced by contact with the subject animal skin, from a first, extended position, to a second retracted position in alignment with the proximal surface 22, releases the needle mount to allow injection to occur. The safety interlock 150 is designed to prevent accidental injection of the human user of the system. Accidental injection of certain veterinary products can cause severe injury of the area accidentally injected. Mounted on hand-held injection device 40''' is solid member 152, a solid member preferably of plastic, which in its first position, extends at least as far as the tip of needle 56. Solid member 152 is urged to a second position, pushed to the tip of the needle hub 57, as indicated by arrow in FIG. 11, when the needle 56 and therefore the solid member 152 comes into contact with the body of the poultry or other animal. When solid member 152 is biased to the second position, it completes the electrical circuit and actuates the pump 100 which permits an injection to take place. This built-in safety device deters accidental, and severely injurious, self-injection. Needle 56 is replaceable. When needle guard solid member 152 reaches a second position, it actuates a Hall effect switch, such as made by the Allegra Corp, of Worchester, Mass., internal of the hand-held injection device 40''' which controls administration. This Hall effect switch, shown in detail at 31 in FIG. 13, is wired in conjunction with the trigger 42 on the hand-held injection device 40''', making it necessary for the trigger 42 to be depressed in order for the switch at the solid member 152 to work. This feature adds materially to the safety and reduced fatigue of the operator, as well as the speed of operation since the operator can depress the trigger 42 constantly allowing injection to occur automatically and as quickly as solid member 152 is depressed.

Trigger 42 is in electrical communication with pump 100. In an alternate embodiment of hand-held injection device 40''' trigger 42 must be depressed, and the needle 56 must be fully inserted, to complete the electrical circuit in the Hall effect switch which actuates the pump 100 and results in an injection. This hand-held injection device 40''' has a safety interlock 152. The other embodiments, 40, 40'& 40'' have an emergency stop button 44, although a safety interlock 152 could be used on all embodiments. At this time, a safety interlock is not deemed necessary on hand-held injection device 40 because it is primarily used on the ears of cattle where the needle is parallel to the ear. A safety interlock would not have any animal body part to urge the interlock to it's second, retracted, position. Also at this time, a safety interlock is not deemed necessary on hand-held injection device 40' because this embodiment is primarily used on soft-tissued animals such as poultry where again the safety interlock would not have a substantial body part to urge the interlock to it's second, retracted, position. A dye source is indicated at 60 with its associated tubing 86 which interconnects, again by a quick connect fluid coupler, to conduit tubing 78 that is in fluid communication with hand-held injection device 40'''.

Figure 6:
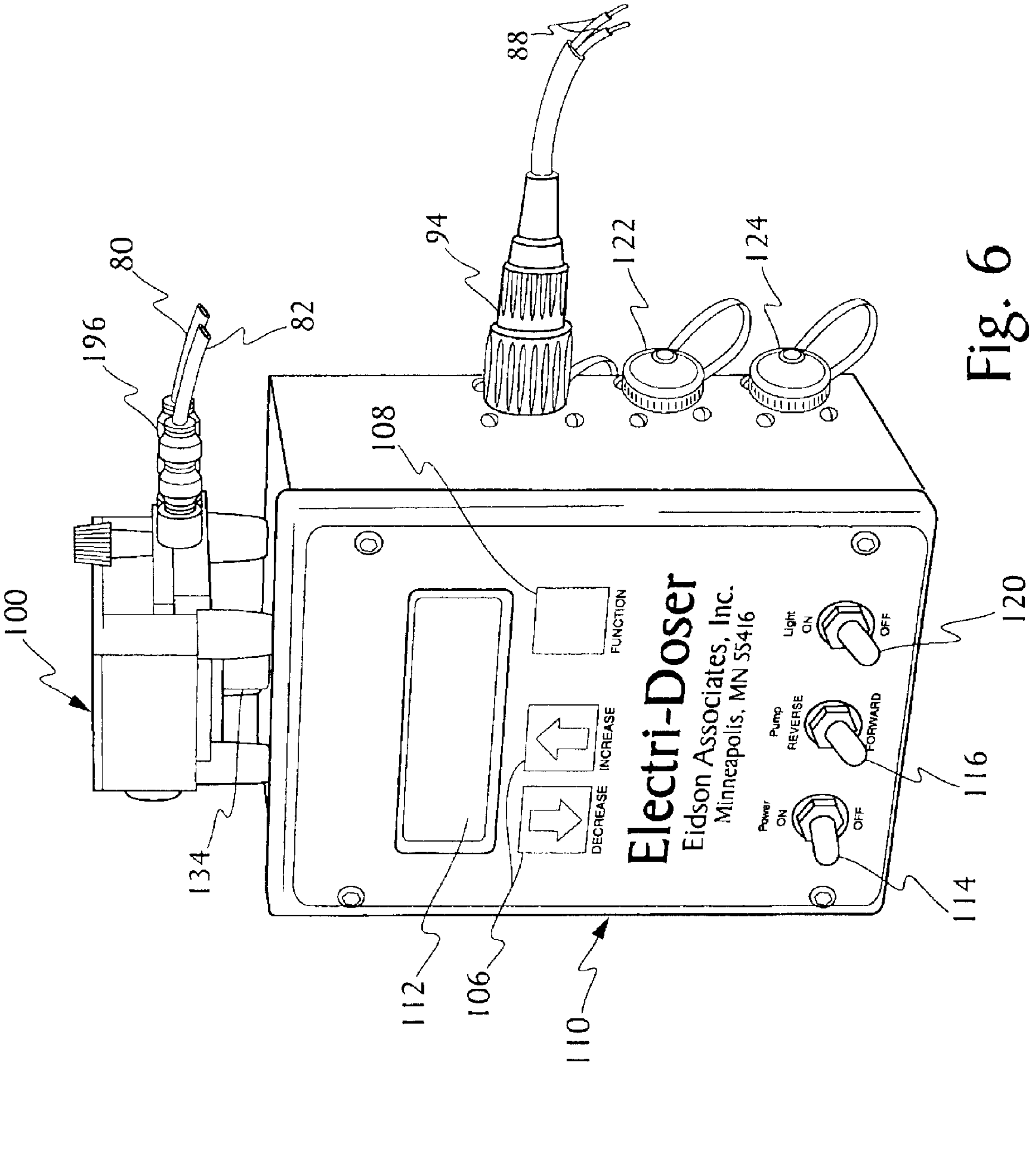
FIG. 6 is a perspective view the control unit of the medicament delivery system of FIG. 1.

FIG. 6 is an external illustration of the control unit 110 of the medicament delivery system 20 of this invention with pump 100 mounted on top. In all embodiments, control unit provides electrical power to hand held units 40 as well as electronic information as set in electronic control to control dosage, dye on/off, and amount, injection count and low medicament level as well as the automatic reverse feature following each injection. A nine-pin amp electrical connector 94 connects the electronic control unit 110 to any of the hand-held injection devices 40. A four-pin amp electrical connector 122 connects the electronic control unit 110 to the dye pump. Another four-pin amp connector 124 connects the control unit 110 to the battery 126. These different amp electrical connectors protect against accidental connection of the wrong device to the outlet at the control unit 110. Display 112 is an LCD display which lights up to illustrate the different modes of the control unit 110, namely, the amount of the selected dosage, the amount of dye used per subject animal, and the count of injections made. The dosage, which is controlled by setting the number of pulses that are emitted by the electronic photo optic sensor 138 to accurately inject the desired dose, depends on the viscosity and temperature of the medicament and must be calculated at each injection session. For example, very low viscosity liquid, such as water, requires 44 pulses per 1.0 milliliter (ml) while on the other hand, dosages of high-viscosity vaccines could require as many as 110 pulses per 1.0 milliliter (ml). The number of pulses in an injection is manually controlled by the up and down arrows 106 on the face of control unit 110, can be set at each injection session. Whether or not to use dye and the amount of dye used can also be selected by control unit 110. The amount of dye to be used can be set in 0.1 second increments. The injection count can be re-set to zero after each injection session by means of the up and down arrows 106. Switches on the face of control unit 110 include an on-off power switch 114, pump switch 116 that controls forward or reverse pump, and light switch 120 which controls power to the head lamp 46.

Being able to switch the pump to reverse enables reclaiming of the sterile serum, or other medicament, that is in the tubing and in the hand-held injection device 40, and pump 100 itself Reversing the pump 100 at the end of each job, by switching upwardly switch 116, effectively retrieves medicament in the system to the container 70 or to be discarded. This procedure can then be followed by switching the pump switch 116 to "forward" to 'clean-in-place' the system 20 by pumping hot detergent water followed by a rinse, or any cleaning procedure outlined by the user. In actual use conditions, an on/off switch such as model # SLP 130A4-16, made by Honeywell, Minneapolis, Minn. power switch has been used although other comparable power switches could be substituted without changing the invention.

Tubing 80 provides medicament to pump 100 while tubing 82 leads from the pump 100 to the particular hand-held injection device 40 selected.

Figure 7:
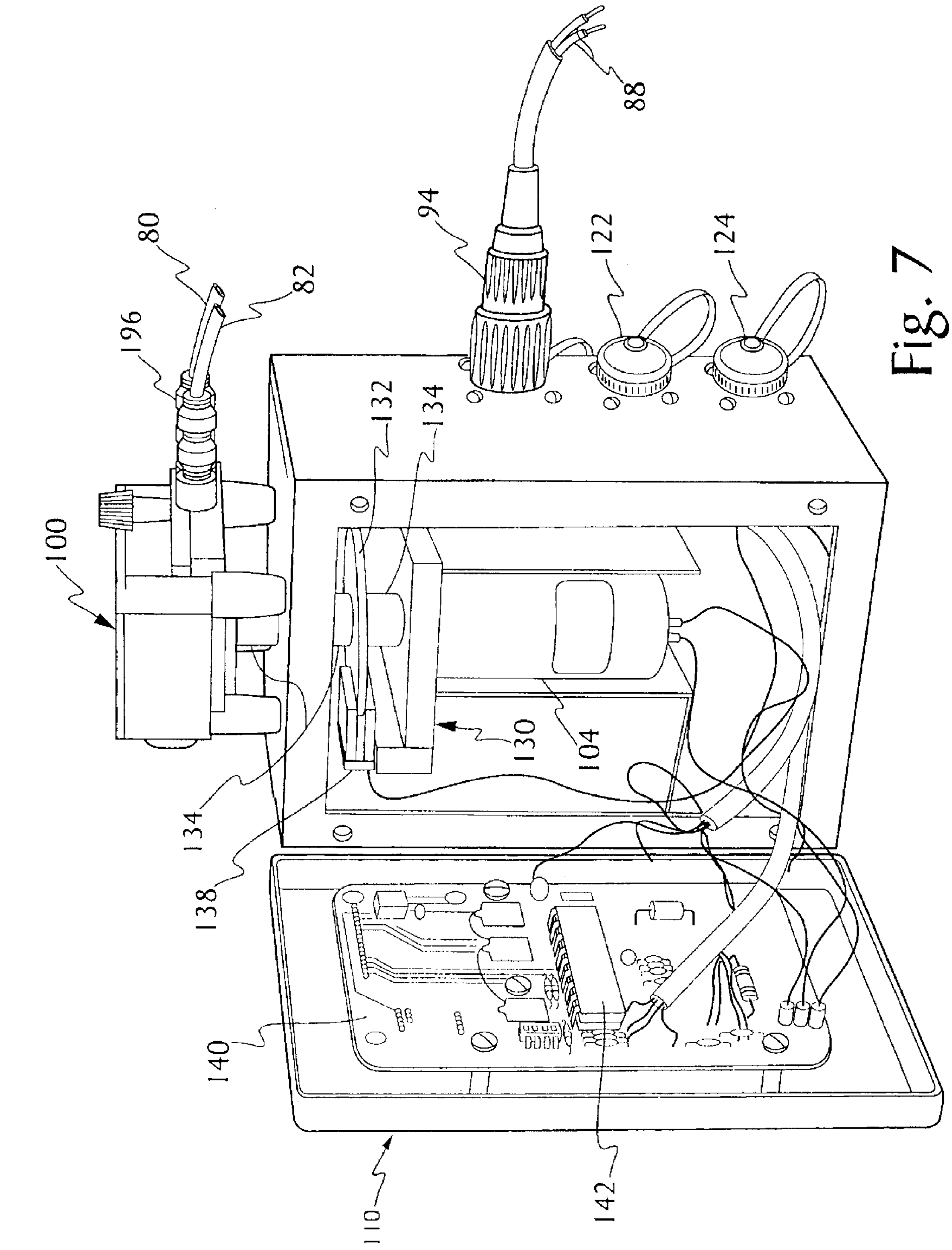
FIG. 7 is a perspective view of the interior of the control unit of FIG. 6.

FIG. 7 is a perspective view of the interior of the control unit of FIG. 6. Electronic dosage control 130 uses a photo-optic unit to control the volume of medicament fluid pumped by pump 100. Pump 100 drives shaft 134 which turns an encoder disc 132 that has slots that are placed at a calibrated distance from one another around the perimeter of circular encoder disc 132. As the encoder disc 132 rotates in response to rotation of drive shaft 134, the slots pass between an emitter and a receiver of a photo-optic sensor 138. The encoder disc 132 passes through the sensor 138. The sensor 138 "counts" the number of slots that pass between an emitter and receiver. The combination of the distance between the slots and the number of slots allowed to pass through the sensor 138 determines the amount of serum that is dispersed. This sensor 138 is wired into a circuit board 140 which includes a micro chip 142 which allows selection and control of the distance the fluid travels in pump 100. This method is preferred because of the ease in changing doses and in view of the changing viscosities of the medicaments used. To change the dose, the user manipulates the function mode by pressing the "Function" key pad 108, of control unit 110. The current number of pulses will flash on the display 112. The pulse count can then be changed by pressing the "UP" or "DOWN" key pad 106 until the correct number of pulses are shown. The press the "Function" keypad 108 to set the correct dose. The LCD display 112 will then stop flashing.

Counter also displayed on LCD display 112, records a dispensed dosage every time any of the hand held units 40 is activated. If desired, the counter keeps a running total of the number of injections given while the veterinary medicament delivery system 20 is turned on. The counter is reset manually by using the down arrow 106. A micro switch liquid crystal display (LCD)unit, made by Curtis Instruments, Inc., 204 Kisco Ave., Mt. Kisco, N.Y. 10549, has been used and works well although other LCD's could be used.

The dosage is set depending on the number of light pulses sensed by the photo optic sensor 138. The user determines how many pulses are equal to 1.0 cc of the injectible medicament and calculates the desired dosage, then determines the number of pulses required for the correct dosage. This setting is reached by, first, pressing the "Function:" key pad 108, at which time the current setting will flash in the LCD 112. Then, by use of the "UP" or DOWN" keypads 106 move the number of pulses to the desired dosage setting at which time the "Function" key pad 108 should be pressed to set the correct dose. The LCD 112 will then stop flashing. The appropriate dose is selected by using the LCD display 112 on control unit 110.

FIG. 8 illustrates an alternate embodiment hand-held injection device 40" used to simultaneously inject two medicaments of similar viscosities. Because these two medicaments may not be mixed, for whatever reason, they are run through separate pumps, 100 and 100' which are interconnected by an extension of drive shaft 134, shown in detail in FIG. 7. Tubing 82 & 82' carries the pumped medicaments separately to hand-held injection device 40" for simultaneous injection. FIG. 9 illustrates the third embodiment hand-hold injection device 40" in the case of desiring to simultaneously inject two medicaments of different viscosities. Again, these two medicaments are hot be to mixed, for whatever reason, and are run through two separate control units, 110 & 110' before being run through tubing 78 & 78' into hand-held injection device 40".

FIG. 10 is a side view of a medicament mixing tube 190 with quick connect fluid connectors 196 at either end. Y-shaped coupling 198 brings together the two medicaments to mixing tube 190. This tubing is inserted in the tubing somewhere between the pump 100 and any of the hand-held injection devices 40, 40', 40", 40'" or 40"". Injectible medicaments from two different sources may be mixed together by use of this mixing tube 190 prior to injection. This is used where the separate injectibles are compatible. In the case where they are not able to be mixed for some reason, the two injection hand-held injection device 40" is used. In use, the mixing tube 190, having a cylindrical barrel chamber 192 with a centrally positioned mixing member, double helix fins 194 shaped as two worm gears rotating in opposite directions, is provided enabling mixing together of two fluids for delivery to any of the hand-held injection devices 40, 40', 40", 40'" or 40"".

Optional marking means is provided in the form of an applicator pad 172 that marks dye onto the subject animal or fowl at the time of injection to conspicuously mark an individual within a group that has been injected.

Hand-Held Injection Device

First hand-held injection device 40, shown in detail in FIG. 1 has a one-piece generally cylindrical housing with a trigger 42 and an emergency stop button 44 mounted on the flattened dorsal surface 41. A red LCD 50 indicates low medicament bottle level while green LCD 48 indicates an injection is in progress. Both are also mounted on the dorsal surface 41. An additional injection in progress LCD 52 is mounted on the distal surface 24 of the hand-held injection device 40, as shown in FIG. 3. Head lamp 46 and dye applicator pad 172 are mounted on the proximal surface of hand-held injection device 40. The needle mount 58, in actual use a Luer lock, receives hollow needle 56. Emergency stop button 44 provides means for preventing accidental injection. The medicament in tubing 84 travels from the pump 100 and is joined by dye in tubing 86 . Both are wound together with power cord 88 into a larger tubing 78 that is received by the distal surface 24 of hand-held injection device 40. Dye applicator pad 172, into which dye is pumped, extends from the hand-held injection device 40 and onto the animal to automatically mark the animal at each injection. Hand-held injection device 40 is especially useful in injection of thin-skinned areas, for example, the ears of cattle.

Hand-held unit 40', shown in FIGS. 2 & 3, is similar in most respects to the first embodiment but adds a dye applicator pad 172. Hand-held injection device 40", shown at FIG. 4, adds an additional hollow needle 56' and needle mount 58'. In this embodiment as illustrated in FIG. 4, has an addition second medicament tubing 82' and power cord 88'. Emergency stop button 44 provides means by which to deter accidental self-injection. The medicament in tubing 82 travels from the pump 100 and is joined by pumped medicament in tubing 82'. Both are wound together with power cord 88 into a larger conduit tubing 78 that is received by the distal surface 24 of hand-held injection device 40". Hand-held injection device 40" is especially useful in injection of poultry.

Hand-held unit 40'", FIG. 5, is similar in most respects to the first, second and third embodiments but the housing of hand-held injection device 40'" is inverted and a pistol grip 30 with the trigger 42 mounted thereon, is added. A safety interlock 150, with solid member 152, is mounted on the proximal surface 22, is used as means for preventing accidental self-injection. The medicament in tubing 82 travels from the pump 100 and is joined by dye in tubing 86. Both are wound together with power cord 88 into a larger conduit tubing 78 that is received by the distal surface 24 of hand-held injection device 40'". Dye applicator pad 172, into which dye is pumped, extends from the hand-held injection device 40'" and onto the animal to automatically mark each animal at each injection. Hand-held injection device 40'" is especially useful in injection of thick skinned animals such as pigs, sheep and cattle in places other than the ear.

Hand-held unit 40"", FIG. 13, is similar in most respects to the first, second, third and fourth embodiments but the housing of hand-held injection device 40"" is a two piece housing with a head portion 32 and a handle portion 34 connected by pivot 36 with the trigger 42 mounted on the handle portion 34. A safety interlock, with solid member 152, is mounted adjacent the hollow needle 56 and is used as means for deterring accidental self-injection. The safety interlock with solid member 152 has a spring 38 to urge the safety interlock solid member 152 into a first position, extending at least as far as the needle 56. Safety interlock with solid member 152 is urged to a second position, pushed to the tip of needle hub 58 as indicated by arrows in FIG. 13, when the needle 56 comes into contact with the body of the poultry or other animal. When safety interlock solid member 152 is biased to the second position, it completes an electrical circuit, a Hall effect switch 31, and actuates the pump 100. The medicament in tubing 82 travels from the pump 100 and is joined by dye in tubing 86. Both are wound together with power cord 88 into a larger conduit tubing 78 that is received by the distal surface 24 of hand-held injection device 40"". Dye applicator pad 172, into which dye is pumped, extends from the hand-held injection device 40"" and onto the animal to automatically mark each animal at each injection. The pivot 36 permits re-positioning of the handle portion 34 relative to the head portion 32 to enable the user to more comfortably fit the injection device 40"" to his or her hand for prolonged use and to facilitate different types of injections as when changing between injecting swine and poultry.

All hand-held units 40, 40', 40", 40'" 40"" are equipped with a hollow needle 56 which is in fluid communication, through injection set tubing 82, with the liquid medicament container 70. When the needle 56 is inserted, the medicament fluid is injected.

In all of the hand-held injection devices 40,40', 40", 40'", & 40"", electrical wiring is connected to port on the control unit 110 by a durable, water resistant electrical amp connectors 94,122,124, such an electrical connector is made by Time Electronic Supply Co., 7803 Green Bay Rd. Suite 302, Bloomington, Minn. 55439. A nine-pin amp connector 94 connects the electronic control unit 110 to the hand-held injection device 40. A four-pin amp connector 122 connects the electronic control unit 110 to the dye pump. Another four-pin amp connector 124 connects the control unit 110 to the battery 126. These different amp connectors protect against accidental connection of the wrong device to the outlet at the control unit 110. A quick connect fluid coupler 196, such as that made by Coulder Products Co., 1001 Westgate Dr. St. Paul, Minn. 55114, connects the injection set tubing 80, 82 to pump 100 and also to mixing tube 190. The quick connect fluid couplers 196 enable the user to select the hand-held injection device 40, 40', 40",40'" or 40"" needed and also to disconnect the tubing when replacement is needed. The quick connect fluid couplers 196 also permits the hand-held injection devices 40, 40', 40", 40'" or 40"" to be disconnected for ease of transportation and storage. Additionally, the quick connect fluid couplers 196 are water proof to a submersible depth of three feet. This connector seals tightly and will prevent dirt and grime from entering the electric contacts that they are protecting.

All hand-held injection devices 40, 40', 40", 40'" & 40"" are also equipped with a light emitting diode as an illuminating head lamp 46, mounted adjacent to the needle 56. A diode such as model HLMP-1503, made by Gilway manufacturer has been used and works well although other light emitting sources could also be used. Head lamp 46, is in electrical communication with battery 126, FIG. 1, provides illumination in low light areas, such as barns, and further attracts attention to the needle 56 to prevent accidental self-injection by user. Poultry are vaccinated in low light in order to keep the birds calm.

Several indicator lights are located on all hand-held injection devices 40, 40', 40", 40'" & 40"". Low serum bottle level is indicated by red LCD signal light 50 set to the count and will light when the bottle is down to approximately 10% of capacity, e.g. in a 250 ml bottle, signal light 50 lights when the bottle is down to about 25. A green LCD 48 mounted on hand-held injection devices 40, 40', 40", 40'", 40"" light to indicate an injection is in progress. These LCDs are in electrical communication with battery 126 by means of wiring 88. The reverse mode is used to retrieve unused medicament at the end of each job thereby reducing waste of medicament. The reverse mode must be set, by means of the "function" button 108 and the down arrow 106 prior to the dosage being set. In actual use conditions, a simple LCD, such as made by model MV-1000 made by Gilway has been used and works well however other LCDs having similar features could be used.

In all of the hand-held injection devices 40, 40', 40", 40'" & 40"", optional dye means is simultaneously dabbed from dye applicator pad 172 to mark the animal or fowl injected, the applicator pad 172 interconnected by dye fluid tubing 86 to a dye container, and is applied in response to again manually pushing main trigger 42 inwardly. There is no separate trigger for controlling the dye function.

Pump

In use, a peristaltic-type pump 100 creates a vacuum within tubing that sucks up the fluid from the medicament container 70 by repetitively compressing and expanding a section of tubing. In actual use conditions, a relatively large bore high density plastic tubing has been used with great success. The size of the tubing bears a direct relationship to the length of time it takes to complete an injection, namely, the larger the tubing, the quicker the injection time. This repetitively compressing and expanding a section of tubing creates a vacuum within the tubing and provides the force to move the fluid from the medicament container through the system to the hand held unit 40, 40', 40", 40'" or 40"" without introducing contamination into the system. In actual use conditions, a peristaltic-type pump such as that made by Barnant Co., 28W 092 Commercial Ave. Barrington, Ill. 60610, has been used although other peristaltic-type pumps could be used. The peristaltic-type pump 100 may additionally be set so that the serum, or other fluid medicament, may be sucked up automatically from the hand-held injection device 40, 40', 40", 40'" or 40"" by manually reversing the pump 100, to prevent waste. The pump 100 is self-priming. The user simply continues to push trigger 42 until serum or other fluid medicament reaches hand-held injection device 40, 40', 40", 40'" 40"". A second peristaltic-type pump 100' may be provided and mounted in a piggy-back manner to force a second fluid medicament through the system at the same rate for delivery through the hand-held injection device 40". Pump 100 is driven by motor 104, FIG. 7, in actual use a 12 volt motor, model # 33GN2732-276 GHS, made by Power Electric Products, 2285 Daniels St. Long Lake, Minn. 515 has been used although other similar 12 volt motors could be used.

Because peristaltic pump 100 works on the premise of displacement, pump 100 accurately and consistently delivers the same dosage. The dose delivered can be formulated by multiplying the inner cross-sectional area of the tubing inside the pump 100 by the distance the tubing is compressed during one cycle of the peristaltic pump. Each time trigger 42 is manually depressed and safety interlock 152 is pushed to its second position in response to needle 56 being fully inserted, the exact dosage is dispensed by pump 100. This increases accuracy of delivery of the dosage and eliminates user error caused by fatigue.

Battery 126 powers motor 104. In actual use conditions, a 12 volt, sealed, lead acid, rechargeable battery, such as model # DG 12-4.2 Guardian made by Douglas Co. has been used although other similar batteries could also be used. One battery charge should be able to power the device 20 through one full day of injections.

Case

Any of the embodiments of veterinary medicament delivery system 20 can be housed in a resilient, light weight material backpack, or other housing, so long as the housing protects the various elements of the veterinary medicament delivery system 20 from dirt and dust. Having the system stored in a backpack enhances portability and storage of the system 20.

Draw-off needle is held in place inside medicament container 70. Tubing 80 is attached at a first end to intake tubing and at a second end to a lead-in tubing for a peristaltic-type pump 100.

Mixing Tube

An optional mixing tube 190, FIG. 10, is provided to mix together two medicaments prior to the medicaments being injected. Mixing tube 190 consists of a chamber 192 with double helix-shaped fins 194 that, when two fluids are introduced through a Y-shaped coupling 198, the two fluids are intermixed as they are pushed down mixing tube before exiting through quick connect fluid coupler 196. As fluids flow through mixing tube 190, the fluids, not shown, pass over a series of stationary, helical-shaped fins 194 which causes the fluids to fold over on themselves. In this manner the fluids are completely mixed in a short distance, e.g. three inches.

Dye Applicator

Dye reservoir 60 has an intake tubing affixed to reservoir 60 that draws up dye in response to a separate dye pump. Dye is drawn into dye tubing 86 in fluid communication with any of the hand-held injection devices 40, 40', 40", 40'" or 40"", but especially with 40'" & 40"". Dye intake tubing 86 draws up dye in response to activation of a dye pump in response to activation of the dye pump by the injection circuit. This pump delivers dye to the applicator pad in increments of 0.1 second for each injection. By setting the dye pump at zero, the dye can be discontinued if desired.

Dye applicator pad 172 is mounted on the proximal surface 22 of hand-held injection device 40, 40', 40", 40'", or 40"" adjacent needle 56 and head lamp 46. Dye applicator pad 172 is in fluid communication with dye reservoir 60. It has been found that dye is dabbed onto the animal's coat or skin simultaneously with the injection works well. The dye applicator pad dabs the dye in 0.1 second increments, depending on the control unit 110 setting. The dye marks the animal injected so that it is easy to distinguish between animals that have been vaccinated or injected and those that have not. This feature is a switched function and can be turned on or off according to the needs of the job, as set by the function key of control unit 110.

Dosage Control

In all embodiments, the selected dosage is administered cleanly and completely, without dripping because the pump 100 is set to automatically reverse at the end of each injection. The amount of this reverse is set into control unit 110 before the dosage is set. This automatic reverse prevents serum, or other fluid medicament, from flowing out of the end of the hand-held injection device 40, 40', 40", 40'", or 40"" due to latent pressure. A quick reverse after each injection prevents drip. It is important, also, to retrieve unused medicament at the end of each injection session. The pump reverse switch is used to retrieve unused medicament at the end of the injection session. The need for reversing fluid flow does not allow for use of a delivery valve because such a valve would prevent any reverse action.

It is an important feature of this system that it does not include a delivery valve. The absence of a delivery valve necessitates a positive, abrupt stop upon the completion of each injection followed by a quick reverse by which drip can be prevented. The injection process, therefore, involves an automatic abrupt stop upon delivery of each dose, immediately followed by a short pre-set reverse sufficient to prevent any drip. This reverse can differ according to the viscosity of the medicament and should be set prior to the start of each injection session, usually 8–10 pulses. By setting this reverse action prior to setting the correct dosage, the precise delivery of each injection is not impaired. The automatic reverse is set using the "Function" keypad 108 and the down arrow 106 on the front of control unit 110.

Electronic dosage control 130 uses a photo-optic sensor 138, shown in detail in FIG. 7, to control the volume of medicament fluid pumped by pump 100. Pump 100 drives shaft 134 that turns an encoder disc 132 that has slots that are placed at a calibrated distance from one another around the perimeter of circular encoder disc 132. As the encoder disc 132 rotates in response to rotation of drive shaft 134, the slots pass between an emitter and a receiver of the photo-optic sensor 138. As the encoder disc 132 passes through the sensor 138, the sensor 138 "counts" the number of slots that pass between an emitter and a receiver inside a dark housing within the control unit 110 adjacent the pump 100. The combination of the distance between the slots and the number of slots allowed to pass through the sensor 138 determines the amount of medicament that is dispersed. This amount is dependent on the viscosity of the medicament and the temperature of the medicament. Setting the required number of pulses by the photo-optic sensor to accurately administer the necessary precise dose is usually accomplished by taking measure of a set number of pulses, maybe 200, then calculating the required pulses for the desired dose. In actual use conditions, the photo-optic encoder disc 132 has 72 slots although other sized discs with other numbers of slots, could be calibrated for use. Since the sensor 138 responds positively in individual slots, it is possible to set the dosage to within 0.0138 milliliter (ml) accuracy. The pump stops abruptly upon the delivery of each dose, then automatically reverses to the number of pre-set pulses in order to stop drip. Usually 10 pulses are sufficient to clear the needle 56 of any drip. This sensor 138 is wired into a circuit board 140 for dosage selection control, one of the functions of control unit 110 of FIGS. 1, 6, 8 & 9 which allows selection and control of the distance the fluid travels in pump 100. To change the dose, manipulate a switch of dosage selection control and select the dose from a selectable dosage LCD display 112 by pressing "Function" keypad 108 until "dose" appears. Then, using the "up" and "down" arrow key pads 106, enter the selected dosage. This number will be flashing on the LCD. To set the dose, touch the "function" keypad 108 at which time the number will stop flashing. Other features of the control unit 110 "function" keypad 108 are: automatic reverse setting, a re-setable counter and a dye selection, shown in detail at FIGS. 1, 6 ,8 & 9. Counter records a dispensed dosage every time the hand-held injection device 40 is activated. Counter keeps a running total of the number of injections given while the veterinary medicament delivery system 20 is turned on. The counter is reset manually by pressing the down arrow 106 on control unit 110. The total is recorded by a liquid crystal display 112 on the control unit 110. A micro switch liquid crystal display unit, made by Curtis Instruments, Inc., 204 Kisco Ave., Mt. Kisco, N.Y. 10549, has been used and works well although other LCD's could be used.

Up and down arrows 106 are used to select from a range of dose settings LCD display 112, the appropriate dose, the chosen dosage setting illuminated by a light. Dosage settings are calibrated into the electronic control unit 110 to accommodate the desired dose. Also shown are three switches: power on/off 114, pump 116 forward/reverse, and head lamp on/off switch 120.

Veterinary medicament delivery system 20 may be cleaned by flushing with hot, e.g. 160° F., detergent/water mixture placed in medicament container 80. To accomplish cleaning, the pump switch on the face of the control unit is set to "forward" in order to circulate cleaning/sanitizing solutions for effective "clean in place". Cleaning practices vary among operators. Flushing with hot detergent water, followed by a clean rinse, is accepted by many who fear harming the vaccines with disinfectants. Others flush with hot detergent water and follow with an alcohol rinse, which, of course, is then rinsed.

All the hand-held injection devices 40, 40', 40", 40'". & 40"" have two signal lights on a top surface thereof, namely red LED 50 signaling low medicament, and green LED 48 indicating injection in progress. On the proximal surface 22 of each hand-held injection device 40, 40', 40", 40'" or 40"" dye applicator pad 172 can be mounted which, when powered on, marks each animal or bird to which medicament is administered.

In the operation of hand-held injection device 40'", FIG. 5, trigger 42 must be depressed, and the needle 56 must be fully inserted into animal or fowl, which pushes safety interlock 152 the tip of the needle hub 58 to complete the electrical circuit to actuate the pump 100 which accomplishes administration of medicament. This double requirement of trigger 42 being depressed and safety interlock solid member 152 pushed to a second position before the medicament is administered reduces the dangers of self-injection. And because the trigger 42 is being depressed, either serially or continually, rather than manually pushing a syringe handle in order to pump the medicament into the animal through the needle and against the pressure of a return spring, this system greatly reduces fatigue and the incidence of repetitive motion injury in the operator. Additionally, use of this system 20 permits greater speed of administration of medicament to the multiplicity of animals or fowl sought to be medicated. Hand-held injection device 40"" also having safety interlock 152, FIG. 13, works similarly to hand-held device 40'".

In the operation of hand-held injection device 40, 40', & 40", trigger 42 must again be depressed for each injection. Emergency stop button 44 enables the user to stop the injection in the case of either piercing the user's skin with the needle 56 or running the needle through the subject animal body, ex. the ear. This deters accidental self-injection and accidental waste of expensive medicament in the case of running the needle through the subject animal body.

Use of the electronic dosage control 130, permits changing of the dosage to be administered and is especially useful when different dosages are to be administered in succession, however, it would be equally useful in situation where a multiplicity of animals or fowl were administered the same dosage of medicament.

Figure 11:
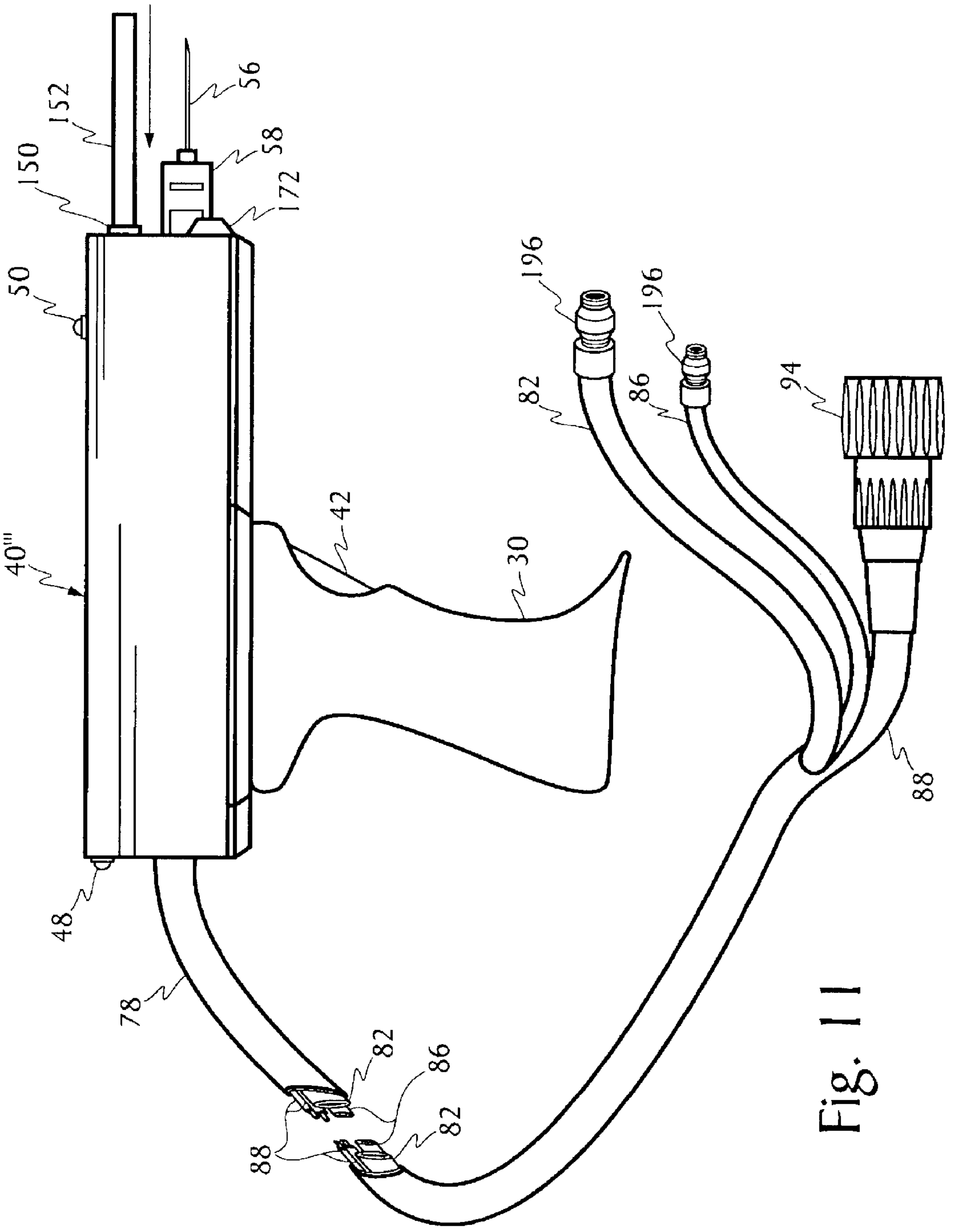
FIG. 11 is a side view of an alternate embodiment pistol grip hand-held unit.
Figure 12:
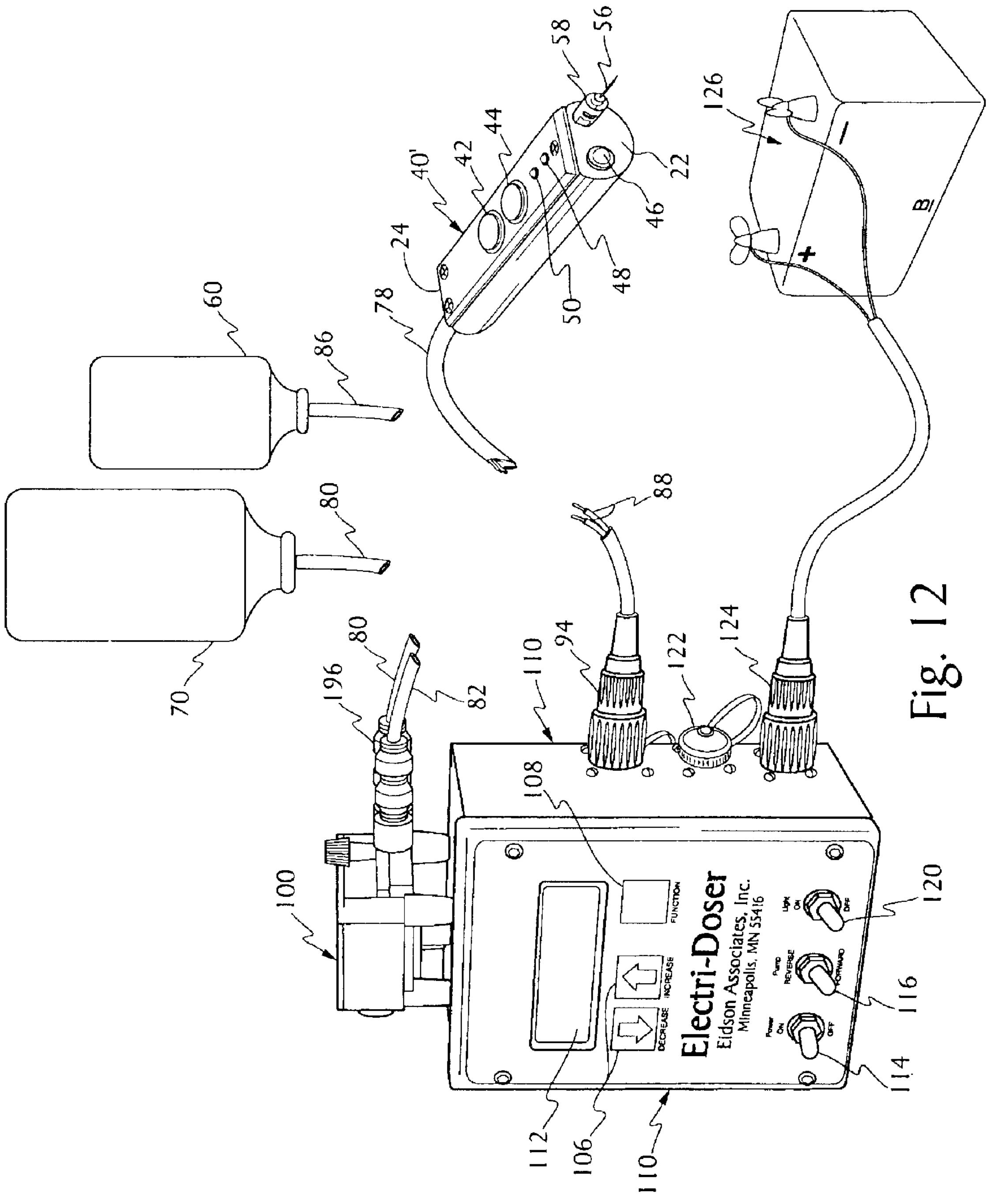
FIG. 12 is a plan view of an alternate embodiment hand-held unit where one medicament is injected and a dye pad applicator is present.

When it is desired that two medicaments are to be administered simultaneously, a mixing tube 190, FIG. 11 may be added between the pump 100, 100' and the hand-held injection device 40. In addition to mixing tube 190, an additional pump 100' and related tubing and T-coupling 198 are used to permit mixing of the two medicaments prior to administration.

Veterinary medicament delivery system 20 may be cleaned by flushing with hot, e.g. 160° F., detergent/water mixture placed in medicament container 80. Cleaning practices vary among operators. Flushing with hot detergent water, followed by a clean rinse, is accepted by many who fear harming the vaccines with disinfectants. Others flush with hot detergent water and follow with an alcohol rinse, which, of course, is then rinsed.

These important features allow for very precise dose from a self-priming, electrically powered pump through a valve-free system which can prevent drip, include important safety features to deter self-injection, automatically mark each animal, total the numbers of injections, retrieve unused medicament and provide for an easy method of internally 'cleaning-in-place' of the system.

Although the present invention has been described in considerable detail with reference to certain preferred versions thereof, other versions are possible. Therefore, the spirit and scope of the appended claims should not be limited to the description of the preferred versions contained herein.

What is claimed is:

1. An automatic veterinary medicament delivery system, for delivery or at leant one fluid medicament to an individual fowl, ovine, porcine or other animal, comprising:

a) a generally cylindrical, valve-free, hand-held injection device for delivery of the medicament;

b) tubing interconnecting said hand-held injection device an fluid communication with at least one liquid medicament;

c) a pump, in fluid communication with both said hand-held injection device and liquid medicament, said pump for forcing a medicament through said tubing to said hand-held injection device for delivery;

d) means for powering said pump; and e) a headlamp, mounted on said hand-held device, for illuminating the injection site.

2. The system of claim 1, further comprising at least one hollow needle for injecting a liquid medicament.

3. The system of claim 2, further comprising a safety interlock, mounted on a distal surface of said hand-held injection device, extending longitudinally therefrom to a point even with said needle tip, said safety interlock urged to a second position, in response to said hand-held injection device being positioned adjacent an animal to be injected, where the needle is inserted completely in said animal body, where an extension of said safety interlock within the housing of said hand-held injection device closes a circuit actuating an injection.

4. The system of claim 1, further comprising means for precisely controlling the amount of a medicament administered.

5. The system of claim 4, said means for precisely controlling the amount of medicament administered further comprise a control unit where the dosage of the medicament to be administered is controlled by setting the number of pulses that are emitted by an electronic photo optic sensor in response to an amount of medicament passing therethrough.

6. The system of claim 5, further comprising signal lights as means for readily indicating when medicament administration is taking place.

7. The system of claim 6, further comprising signal lights as means for indicating when the medicament fluid level is low.

8. The system of claim 1, further comprising an emergency stop button mounted on said hand-held injection device.

9. The system of claim 1, wherein a hand-held injection device further includes:

a) a trigger, in electrical communication with said pump, mounted on a dorsal surface of said device;

b) an emergency stop button mounted on a dorsal surface of said device as means for deterring accidental self-injection of the user; and c)

an injection in progress signal light mounted on said housing of said device.

10. The system of claim 1, wherein a hand-held injection device further includes:

a) a trigger, in electrical communication with said pump, mounted on a dorsal surface of said device;

b) an emergency stop button mounted on a dorsal surface of said device as means for accidental self-injection of the user;

c)

an injection in progress signal light mounted on said housing of said device; and d optional dye marking means for conspicuously marking an animal injected, simultaneously with the injection.

11. The system of claim 1, wherein a hand-held injection device further includes:

a) a trigger, in electrical communication with said pump, mounted on a pistol grip handle mounted on said device;

b) a safety interlock mounted on the proximal surface of said device as means for deterring accidental self-injection of the user;

c) an injection in progress light mounted on said housing of said device; and c optional dye marking means for conspicuously marking an animal injected, simultaneously with the injection.

12. The system of claim 1, wherein said hand-held injection device selected is installed for fluid connection with the system by means of a quick connect fluid coupler connecting to said pump.

13. The system of claim 12, wherein said hand-held injection device selected is installed for electrical connection by means of an electrical connector to said control unit for powering said selected hand-held injection device.

14. The system of claim 13, wherein said control unit permits selecting appropriate doses to be delivered by said selected hand-held injection device.

15. The system of claim 14, said control unit further comprises:

a) a photo-optic sensor to control the volume of medicament fluid pumped by said pump;

b) a circular encoder disc, having slots formed in said encoder disc placed at a calibrated distance from one another around the perimeter of said encoder disc;

c) a drive shaft, driven by said pump, for driving said encoder disc wherein said slots pass between an emitter and a receiver of said photo-optic sensor permitting calibration of the amount of said medicament dispersed.

16. The system of claim 1, wherein said headlamp further comprises a light emitting diode.

17. An automatic veterinary medicament delivery system, for delivery of at least one fluid medicament to an individual fowl, ovine, porcine or other animal within a group, comprising:

a) a generally cylindrical, valve-free, hand-held injection device;

b) tubing interconnecting said hand-held injection device in fluid communication with at least one liquid medicament;

c) a pump, in fluid communication with both said hand-held injection device and liquid medicament, said pump for forcing a medicament through said tubing to said hand-held injection device for delivery;

d) means for powering said pump;

e) a headlamp, mounted on said hand-held device, for illuminating the injection site;

f) an emergency atop button mounted on said hand-held injection device as means for deterring accidental self-injection by a user of said system; and g) a control unit where the dosage of the medicament to be administered is controlled by setting the number of pulses that are emitted by an electronic photo optic sensor in response to an amount of medicament passing therethrough as means for precisely controlling the amount of a medicament administered.

18. The system of claim 17, further comprising signal lights as means for readily indicating when in injection is taking place.

19. The system of claim 18, further comprising signal lights as means for indicating when the medicament fluid level is low.

20. The system of claim 17, further comprising at least one hollow needle for injecting a liquid medicament.

21. An automatic veterinary medicament delivery system, for delivery of at least one fluid medicament to an individual fowl, ovine, porcine or other animal within a group, comprising:

a) A generally cylindrical, valve-free, hand-held injection device having at least one hollow needle for injecting a liquid, b) tubing interconnecting said hand-held injection device in fluid communication with at least one liquid medicament;

c) a pump, in fluid communication with both said hand-held injection device and liquid medicament, said pump for forcing a medicament through said tubing to said hand-held injection device for delivery;

d) means for powering said pump;

e) a headlamp, mounted on said hand-held device, for illuminating the injection site;

f) a safety interlock, mounted on said proximal surface of said hand-held injection device, extending longitudinally therefrom to a point even with said needle tip, said safety interlock urged to a second position, in response to said hand-held injection device being positioned adjacent an animal to be injected, where the noodle is inserted completely in said animal body, where an extension of said safety interlock within the housing of said hand-held injection device closes a circuit actuating an injection as means for deterring accidental self-injection by a user of maid system; and g a control unit where the dosage of the medicament to be administered is controlled by setting the number of pulses that are emitted by an electronic photo optic sensor in response to an amount of medicament passing therethrough as means for precisely controlling the amount of a medicament administered.

22. The system of claim 21, wherein said control unit further comprises:

a) a photo-optic sensor to control the volume of medicament fluid pumped by said pump;

b) a circular encoder disc, having slots formed in said encoder disc placed at a calibrated distance from one another around the perimeter of said encoder disc;

c) a drive shaft, driven by said pump, for driving said encoder disc wherein said slots pass between an emitter and a receiver of said photo-optic sensor permitting calibration of the amount of said medicament dispersed.

23. The system of claim 21, further comprising signal light as means for readily indicating when in injection is taking place.

24. The system of claim 23, further comprising signal lights as means for indicating when the medicament fluid level is low.

25. An automatic veterinary medicament delivery system, for delivery of fluid medicaments to an individual animal or fowl, comprising:

a hand-held injection device for delivery of the medicament;

a source of medicament;

tubing interconnecting said injection device and said source of medicament;

a pump in fluid communication with both said injection device and said source of medicament, for forcing the medicament through said tubing from said medicament source to said injection device for delivery;

electronic dosage control means for selecting a dosage of medicament to be delivered by the injection device from a range of dosages;

means for powering said pump;

a headlamp mounted on a housing of said hand-held injection device for illuminating the area to be injected;

a container for said pump, tubing, medicament source and injection device, protecting said system from dirt and dust and simplifying transportation;

wherein the electronic dosage control means comprises;

a circular-shaped encoder disk having slots formed in the periphery thereof; and a light source mounted adjacent said encoder disk such that light emitted from said light source shines through said slots, said emitted light sensed by a photoelectric sensor in response to movement of the pomp providing means for measuring amount of dose delivered by the pump.

26. An automatic veterinary medicament delivery system, for delivery of at least one fluid medicament to an individual fowl, ovine, or other animal within a group, comprising:

a) a hand-held injection device for delivery of the medicament through a hollow needle is housed within a head portion of said device;

b) said injection device further including a housing with a head portion and a handle portion, said portions being pivotally connected c a source of medicament;

d means for measuring the amount of medicament delivered;

e) tubing interconnecting said device and said source of medicament;

f) a self-priming peristaltic pump, external to said device, in fluid communication with both said device and said source of medicament, for forcing the medicament through said tubing from said medicament source to said device for delivery; and g) means for powering said pump.

27. The system of claim 26, further comprising a spring-loaded retractable safety interlock adjacent said needle wherein spring biasing means urges said safety interlock into a first position extending longitudinally at least as far as the tip of said needle and means are further provided for overcoming said spring biasing means, urging said safety interlock into a second position wherein said needle is extended longitudinally beyond said safety interlock and closing an electrical switch which actuates said pump causing release of fluid through said needle.

28. The system of claim 27, wherein a trigger is mounted on the housing said trigger in electrical communication with the pump and in conjunction with the safety interlock switch, wherein when said trigger is depressed, said safety interlock is biased to a second position actuating said switch and completes the electrical circuit and actuates said pump to power the injection device to deliver medicament to the animal or fowl to be injected, said trigger deterring accidental self-injection.

29. The injection device of claim 26, wherein said housing, having said head portion and said handle portion with said pivot, may be adapted for a linear alignment of said head portion and said handle portion to facilitate different positions for delivery of medicament such that re-positioning said housing changes the angle of injection.

30. A method of delivering a fluid medicament to an individual fowl, ovine, porcine, or other animal within a group, comprising the steps of:

a) providing a generally cylindrical, valve-free, hand-held injection device having at least one hollow needle far injecting a liquid;

b) interconnecting said injection device with tubing for fluid communication with a liquid medicament;

c) forcing the medicament by a pump through tubing to said injection device for delivery;

d) powering said pump; and e) mounting a head lamp on said injection device for illuminating the area of injection.

31. The method of claim 30, wherein said method of deterring accidental self-injection of user further includes the steps of:

a) providing a two-step injection process that must be completed before injection takes place, further comprising:

i) injecting said hollow needle fully into subject animal; and ii) depressing a trigger on said hand-held injection device handle.

32. The method of claim 30, wherein said method of deterring accidental self-injection of user further includes the step of providing an emergency stop button on said hand-held injection device.

33. The method of claim 30, wherein said method of deterring accidental self-injection of user further includes the step of providing a safety interlock, mounted on a proximal surface of said hand-held injection device, said safety interlock extending longitudinally therefrom to a point even with said needle tip, said safety interlock urged to a second position, in response to said hand-held injection device being positioned adjacent an animal to be injected, where the needle is inserted completely in said animal body, where an extension of said safety interlock within the housing of said hand-held injection device closes a circuit actuating an injection.

34. The method of claim 30, further comprising the atop of providing a control unit for precisely controlling the amount of a medicament administered, further comprising the step of;

a) providing a photo-optic sensor to control the volume of medicament fluid pumped by said pump;

b) providing a circular encoder disc, having slots formed in said encoder disc at a calibrated distance from one another around the perimeter of said encoder disc; and c) providing a drive shaft, driven by said pump, for driving said encoder disc wherein said slots pass between an emitter and a receiver of said photo-optic sensor permitting calibration of the amount of said medicament dispersed.

35. An automatic veterinary medicament delivery system, for delivery of fluid medicaments to an individual animal or fowl, comprising;

a hand-held injection device for delivery of the medicament;

a source of medicament;

tubing interconnecting said injection device and said source of medicament;

a self printing peristaltic pump, external to said injection device, in fluid communication with both said injection device and said source of medicament, for forcing the medicament through said tubing from said medicament source to said injection device for delivery;

means for powering said pump;

a container for said pump, tubing, medicament source and injection device, protecting said system from dirt and dust and simplifying transportation, and a headlamp mounted on the housing of said hand-held injection device, for illumination of the area to be injected.

36. The system of claim 35, wherein the means for selecting a dosage comprises an electronic dosage control means adjacent to the pump.

37. The system of claim 36, wherein the dosage control means further comprises a photoelectric sensor that enumerates the amount of medicament being delivered.

38. The system of claim 36, wherein the control means is an electronic dosage control system comprising:

a circular-shaped encoder disk having slots formed in the periphery thereof; and a light source mounted adjacent said encoder disk such that light emitted from said light source shines through said slots, said emitted light sensed by said sensor in response to movement of the pump providing means for measuring amount of dose delivered by the pump.

39. The electronic dosage control panel of claim 36, further comprising a battery charge indicator light.

40. The system of claim 36, wherein the electronic dosage control means further comprises an automatic digital counter to record total injections.

41. The system of claim 36, wherein the electronic dosage control means further comprise a pump reverse switch.

42. The system of claim 36, wherein the electronic dosage control means further comprises medicament low level indicator light.

43. The system of claim 36, wherein the electronic dosage control means further comprises dye low level indicator light.

44. The system of claim 35, further comprising a green LED indicator light indicating injection in progress.

45. The system of claim 35, further comprising signal lights mounted on said injection device for indicating low medicament fluid level.

46. The system of claim 35, wherein said injection device further comprises a housing with a head portion, handle portion and a dye nozzle for delivery of said medicament to an external surface of the animal or fowl to be medicated, said dye nozzle mounted on the head portion of said injection device, a dye reservoir, in fluid communication with said dye nozzle, and an electrically powered dye pump for drawing dye from said dye reservoir into tubing for fluid communication with said dye nozzle for concurrent delivery of dye to mark an individual injected.

47. The system of claim 35, wherein said container is a backpack.

48. The system of claim 35, wherein at least one hollow needle is housed with the head portion and in fluid communication with the medicament source.

49. The system of claim 48, wherein a safety interlock solid member is adjacent said at least one needle and when urged to a second position complete an electrical circuit to actuate the pump.

50. The system of claim 49, wherein a trigger is mounted on the housing, said trigger in electrical communication with the pump and in conjunction with said safety interlock, wherein when said trigger is depressed said safety interlock is biased to a second position actuating said switch and completes the electrical circuit and actuates said pump to power the injection device to deliver medicament to the animal or fowl to be injected.

51. The system of claim 35, further comprising electrical wiring that is connected to both the medicament source and a signal light mounted on the injection device to signal low fluid level in the medicament source.

52. The system of claim 35, further comprising means for selecting a dosage of medicament to be delivered by the injection device from a range of dosages.

53. The system of claim 35, wherein said headlamp further comprising illumination means positioned adjacent said needle, for providing illumination in low-light areas and warning the user to avoid self-injection.

54. The system of claim 35, wherein said self-priming peristaltic primp is pre-set to reverse at the end of each injection to eliminate drip and to ensure accuracy of dose.

55. The system of claim 35, wherein said self-priming peristaltic pump is pre-set to reverse to retrieve unused medicament.

* * * * *